United States Patent
Band et al.

(10) Patent No.: US 12,187,780 B2
(45) Date of Patent: Jan. 7, 2025

(54) CAR T-CELLS COMPRISING INACTIVATED CBL AND CBL-B GENES

(71) Applicant: BOARD OF REGENTS OF THE UNIVERSITY OF NEBRASKA, Lincoln, NE (US)

(72) Inventors: Hamid Band, Omaha, NE (US); Vimla Band, Omaha, NE (US); Fany Iseka, Omaha, NE (US); Bhopal Mohapatra, Omaha, NE (US); Matthew Storck, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 1031 days.

(21) Appl. No.: 16/484,504

(22) PCT Filed: Feb. 23, 2018

(86) PCT No.: PCT/US2018/019408
§ 371 (c)(1),
(2) Date: Aug. 8, 2019

(87) PCT Pub. No.: WO2018/156886
PCT Pub. Date: Aug. 30, 2018

(65) Prior Publication Data
US 2019/0374578 A1    Dec. 12, 2019

Related U.S. Application Data

(60) Provisional application No. 62/473,802, filed on Mar. 20, 2017, provisional application No. 62/462,641, filed on Feb. 23, 2017.

(51) Int. Cl.
| | |
|---|---|
| *A61K 35/17* | (2015.01) |
| *A61K 39/00* | (2006.01) |
| *C07K 14/705* | (2006.01) |
| *C07K 14/725* | (2006.01) |
| *C07K 16/28* | (2006.01) |
| *C07K 16/30* | (2006.01) |
| *C07K 16/32* | (2006.01) |
| *C12N 5/0783* | (2010.01) |
| *C12N 15/113* | (2010.01) |

(52) U.S. Cl.
CPC .... *C07K 14/70521* (2013.01); *A61K 39/4611* (2023.05); *A61K 39/4631* (2023.05); *A61K 39/464406* (2023.05); *A61K 39/464412* (2023.05); *A61K 39/464471* (2023.05); *C07K 14/7051* (2013.01); *C07K 14/70578* (2013.01); *C07K 16/2803* (2013.01); *C07K 16/3061* (2013.01); *C07K 16/3084* (2013.01); *C07K 16/32* (2013.01); *C12N 5/0638* (2013.01); *C12N 15/1137* (2013.01); *C07K 2317/622* (2013.01); *C07K 2317/92* (2013.01); *C07K 2319/03* (2013.01); *C12N 2310/14* (2013.01)

(58) Field of Classification Search
None
See application file for complete search history.

(56) References Cited

U.S. PATENT DOCUMENTS

2016/0312183 A1    10/2016    Gu et al.

FOREIGN PATENT DOCUMENTS

| WO | 2014/201021 A2 | 12/2014 | |
|---|---|---|---|
| WO | 2015/124715 A1 | 8/2015 | |
| WO | WO-2017120996 A1 * | 7/2017 | ......... A61K 31/7088 |

OTHER PUBLICATIONS

Whilding et al. Immunotherapy 2015 7(3), 229-241.*
Nozawa et al. Neurol Med Chir (Tokyo) 59, 89-97, 2019.*
Cartellier et al., J Biomedicine and Biotechnology vol. 2010, Article ID 956304, 2010.*
Chicaybam et al., International Reviews of Immunology, 30:5-6, 294-311, 2011.*
Mohapatra, et al., "An essential role of CBL and CBL-B ubiquitin ligases in mammary stem cell maintenance" Development (2017) 144(6):1072-1086.
Duan, et al., "Negative regulation of EGFR-Vav2 signaling axis by Cbl ubiquitin ligase controls EGF receptor-mediated epithelial cell adherens junction dynamics and cell migration" J. Biol. Chem. (2011) 286(1):620-33.
Mohapatra, et al., "Protein tyrosine kinase regulation by ubiquitination: critical roles of Cbl-family ubiquitin ligases" Biochim Biophys Acta (2013) 1833(1):122-39.
Naramura, et al., "c-Cbl and Cbl-b regulate T cell responsiveness by promoting ligand-induced TCR down-modulation" Nat. Immunol. (2002) 3(12):1192-9.
Goetz, et al., "A novel CBL-Bflox/flox mouse model allows tissue-selective fully conditional CBL/CBL-B double-knockout: CD4-Cre mediated CBL/CBL-B deletion occurs in both T-cells and hematopoietic stem cells" Oncotarget. (2016) 7(32):51107-51123.
Naramura, et al., "Rapidly fatal myeloproliferative disorders in mice with deletion of Casitas B-cell lymphoma (Cbl) and Cbl-b in hematopoietic stem cells" Proc. Natl. Acad. Sci. (2010) 107(37):16274-9.
Naramura, et al., "Altered thymic positive selection and intracellular signals in Cbl-deficient mice" Proc. Natl. Acad. Sci. (1998) 95(26):15547-52.

(Continued)

*Primary Examiner* — Sharon X Wen

(74) *Attorney, Agent, or Firm* — Robert C. Netter, Jr.; Dann, Dorfman, Herrell & Skillman

(57) ABSTRACT

Methods and compositions for treating cancer, particularly improved CAR-T methods, are disclosed.

8 Claims, 7 Drawing Sheets
Specification includes a Sequence Listing.

(56) References Cited

OTHER PUBLICATIONS

An, et al., "Loss of Cbl and Cbl-b ubiquitin ligases abrogates hematopoietic stem cell quiescence and sensitizes leukemic disease to chemotherapy" Oncotarget (2015) 6(12):10498-509.
Lutz-Nicoladoni, et al., "Reinforcement of cancer immunotherapy by adoptive transfer of cblb-deficient CD8+ T cells combined with a DC vaccine" Immunol. Cell Biol. (2012) 90(1):130-4.
Kang, J.M., et al., "CBL enhances breast tumor formation by inhibiting tumor suppressive activity of TGF-β signaling" Oncogene (2012) 31(50):5123-31.
Hinrichs, C.S., "Molecular Pathways: Breaking the Epithelial Cancer Barrier for Chimeric Antigen Receptor and T-cell Receptor Gene Therapy" Clin. Cancer Res. (2016) 22(7):1559-64.
Zha, Y., et al., "An adenoviral vector encoding dominant negative Cbl lowers the threshold for T cell activation in post-thymic T cells" Cell. Immunol. (2007) 247(2):95-102.

\* cited by examiner

GGGAAGCTTGCCACCATGGCCTTACCAGTGACCGCCTTGCTCCTGCCGCTGGCCTTGCTGCTCCA
CGCCGCCAGGCCGGATATCCAGATGACCCAGTCCCCGAGCTCCCTGTCCGCCTCTGTGGGCGATA
GGGTCACCATCACCTGCCGTGCCAGTCAGGATGTGAATACTGCTGTAGCCTGGTATCAACAGAAA
CCAGGAAAAGCTCCGAAACTACTGATTTACTCGGCATCCTTCCTCGAGTCTGGAGTCCCTTCTCG
CTTCTCTGGTTCAGATCTGGGACGGATTTCACTCTGACCATCAGCAGTCTGCAGCCGGAAGACT
TCGCAACTTATTACTGTCAGCAACATTATACTACTCCTCCCACGTTCGGACAGGGTACCAAGGTG
GAGATCAAAGGTGGTGGTGGTTCTGGTGGTGGTGGTTCTGGCGGCGGCGGCTCCGAGGTTCAGCT
GGTGGAGTCTGGCGGTGGCCTGGTGCAGCCAGGGGGCTCACTCCGTTTGTCCTGTGCAGCTTCTG
GCTTCAACATTAAAGACACCTATATACACTGGGTGCGTCAGGCCCCGGGTAAGGGCCTGGAATGG
GTTGCAAGGATTTATCCTACGAATGGTTATACTAGATATGCCGATAGCGTCAAGGGCCGTTTCAC
TATAAGCGCAGACACATCCAAAAACACAGCCTACCTGCAGATGAACAGCCTGCGTGCTGAGGACA
CTGCCGTCTATTATTGTTCTAGATGGGGAGGGGACGGCTTCTATGCTATGGACGTGTGGGGTCAA
GGAACCCTGGTCACCGTCTCCTCGGAGCCCAAATCTTGTGACAAAACTCACACATGCCCACCGTG
CCCAGCACCTGAGTCGGGGACCGTCAGTCTTCCTCTTCCCCCCAAAACCCAAGGACACCCTCA
TGATCCCCCGGACCCCTGAGGTCACATGCGTGGTGGTGGACGTGAGCCACGAAGACCCTGAGGTC
AAGTTCAACTGGTACGTGGACGGCGTGGAGGTGCATAATGCCAAGACAAAGCCGCGGGAGGAGCA
GTACAACAGCACGTACCGTGTGGTCAGCGTCCTCACCGTCCTGCACCAGGACTGGCTGAATGGCA
AGGAGTACAAGTGCAAGGTCTCCAACAAAGCCCTCCCAGCCCCCATCGAGAAAACCATCTCCAAA
GCCAAAGGGCAGCCCCGAGAACCACAGGTGTACACCCTGCCCCCATCCCGGGAGGAGATGACCAA
GAACCAGGTCAGCCTGACCTGCCTGGTCAAAGGCTTCTATCCCAGCGACATCGCCGTGGAGTGGG
AGAGCAATGGGCAGCCGGAGAACAACTACAAGACCACGCCTCCCGTGCTGGACTCCGACGGCTCC
TTCTTCCTCTATAGCAAGCTCACCGTGGACAAGAGCAGGTGGCAGCAGGGGAACGTCTTCTCATG
CTCCGTGATGCATGAGGCTCTGCACAACCACTACACGCAGAAGAGCCTCTCCCTGTCCCCGGGTA
AAGGATCCGGG

Figure 3A

MALPVTALLLPLALLLHAARPDIQMTQSPSSLSASVGDRVTITCRASQDVNTAVAWYQQKPGKAPKLL
IYSASFLYSGVPSRFSGSRSGTDFTLTISSLQPEDFATYYCQQHYTTPPTFGQGTKVEIKGGGGSGGG
GSGGGGSEVQLVESGGGLVQPGGSLRLSCAASGFNIKDTYIHWVRQAPGKGLEWVARIYPTNGYTRYA
DSVKGRFTISADTSKNTAYLQMNSLRAEDTAVYYCSRWGGDGFYAMDVWGQGTLVTVSSEPKSCDKTH
TCPPCPA????GPSVFLFPPKPKDTLM???TPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNVFSCSVMH
EALHNHYTQKSLSLSPGKGF

Figure 3B

GGGAAGCTTGCCACCATGGCCTTACCAGTGACCGCCTTGCTCCTGCCGCTGGCCTTGCTGCTCCACGC
CGCCAGGCCGGACATCCAGATGACACAGACTACATCCTCCCTGTCTGCCTCTCTGGGAGACAGAGTCA
CCATCAGTTGCAGGGCAAGTCAGGACATTAGTAAATATTTAAATTGGTATCAGCAGAAACCAGATGGA
ACTGTTAAACTCCTGATCTACCATACATCAAGATTACACTCAGGAGTCCCATCAAGGTTCAGTGGCAG
TGGGTCTGGAACAGATTATTCTCTCACCATTAGCAACCTGGAGCAAGAAGATATTGCCACTTACTTTT
GCCAACAGGGTAATACGCTTCCGTACACGTTCGGAGGGGGGACTAAGTTGGAAATAACACGGGCTGAT
GCTGCACCAACTGTATCCATCTTCCCACCATCCAGTAATGGTGGTGGTGGTTCTGGTGGTGGTGGTTC
TGGCGGCGGCGGCTCCGAGGTGAAACTGCAGGAGTCAGGACCTGGCCTGGTGGCGCCCTCACAGAGCC
TGTCCGTCACATGCACTGTCTCAGGGGTCTCATTACCCGACTATGGTGTAAGCTGGATTCGCCAGCCT
CCACGAAAGGGTCTGGAGTGGCTGGGAGTAATATGGGGTAGTGAAACCACATACTATAATTCAGCTCT
CAAATCCAGACTGACCATCATCAAGGACAACTCCAAGAGCCAAGTTTTCTTAAAAATGAACAGTCTGC
AAACTGATGACACAGCCATTTACTACTGTGCCAAACATTATTACTACGGTGGTAGCTATGCTATGGAC
TACTGGGGTCAAGGAACCTCAGTCACCGTCTCCTCAGAGCCCAAATCTTGTGACAAAACTCACACATG
CCCACCGTGCCCAGCACCT??A?TC??GGGACCGTCAGTCTTCCTCTTCCCCCCAAAACCCAAGGACA
CCCTCATGATC?CCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCGCGGGAGGAGCA
GTACAACAGCACGTACCGTGTGGTCAGCGTCCTCACCGTCCTGCACCAGGACTGGCTGAATGGCAAGG
AGTACAAGTGCAAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAGGAGATGACCAAGAACCAGGT
CAGCCTGACCTGCCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTCTTCCTCTATAGC
AAGCTCACCGTGGACAAGAGCAGGTGGCAGCAGGGGAACGTCTTCTCATGCTCCGTGATGCATGAGGC
TCTGCACAACCACTACACGCAGAAGAGCCTCTCCCTGTCCCCGGGTAAAGGATCCGGG

Figure 3C

MALPVTALLLPLALLLHAARPDIQMTQTTSSLSASLGDRVTISCRASQDISKYLNWYQQKPDGTVKLL
IYHTSRLHSGVPSRFSGSGSGTDYSLTISNLEQEDIATYFCQQGNTLPYTFGGGTKLEITRADAAPTV
SIFPPSSNGGGGSGGGGSGGGGSEVKLQESGPGLVAPSQSLSVTCTVSGVSLPRYGVSWIRQPPRKGL
EWLGVIWGSETTYYNSALKSRLTIIKDNSKSQVFLKMNSLQTDDTAIYYCAKHYYGGSYAMDYWGQG
TSVTVSSEPKSCDKTHTCPPCPA????GPSVFLFPPKPKDTLM???TPEVTCVVVDVSHEDPEVKFNW
YVDGVEVHNAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGKGF

Figure 3D

```
GGGAAGCTTGCCACCATGGCCTTACCAGTGACCGCCTTGCTCCTGCCGCTGGCCTTGCTGCTCCACGC
CGCCAGGCCCGAGAACCAGATGACCCAGAGCCCCAGCAGCCTGAGCGCCAGCGTGGGCGACAGAGTGA
CCATGACCTGCAGAGCCAGCAGCAGCGTGAGCAGCAGCTACCTGCACTGGTACCAGCAGAAGAGCGGC
AAGGCCCCCAAGGTGTGGATCTACAGCACCAGCAACCTGGCCAGCGGCGTGCCCAGCAGATTCAGCGG
CAGCGGCAGCGGCACCGACTACACCCTGACCATCAGCAGCCTGCAGCCCGAGGACTTCGCCACCTACT
ACTGCCAGCAGTACAGCGGCTACCCCATCACCTTCGGCCAGGGCACCAAGGTGGAGATCAAGGGTGGT
GGTGGTTCTGGTGGTGGTGGTTCTGGCGGCGGCGGCTCCCAGGTGCAGCTGCAGGAGAGCGGCCCCGG
CCTGGTGAAGCCCAGCCAGACCCTGAGCATCACCTGCACCGTGAGCGGCTTCAGCCTGGCCAGCTACA
ACATCCACTGGGTGAGACAGCCCCCCGGCAAGGGCCTGGAGTGGCTGGGCGTGATCTGGGCCGGCGGC
AGCACCAACTACAACAGCGCCCTGATGAGCAGACTGACCATCAGCAAGGACAACAGCAAGAACCAGGT
GTTCCTGAAGATGAGCAGCCTGACCGCCGCCGACACCGCCGTGTACTACTGCGCCAAGAGAAGCGACG
ACTACAGCTGGTTCGCCTACTGGGGCCAGGGCACCCTGGTGACCGTGAGCAGCGAGCCCAAATCTTGT
GACAAAACTCACACATGCCCACCGTGCCCAGCACCTGCAGTCCCGGGACCGTCAGTCTTCCTCTTCCC
CCCAAAACCCAAGGACACCCTCATGATCCCCCGGACCCCTGAGGTCACATGCGTGGTGGTGGACGTGA
GCCACGAAGACCCTGAGGTCAAGTTCAACTGGTACGTGGACGGCGTGGAGGTGCATAATGCCAAGACA
AAGCCGCGGGAGGAGCAGTACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCCCAGCCCCCATCGAGAAAA
CCATCTCCAAAGCCAAAGGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCAGCGACATCGCCGTGGA
GTGGGAGAGCAATGGGCAGCCGGAGAACAACTACAAGACCACGCCTCCCGTGCTGGACTCCGACGGCT
CCTTCTTCCTCTATAGCAAGCTCACCGTGGACAAGAGCAGGTGGCAGCAGGGGAACGTCTTCTCATGC
TCCGTGATGCATGAGGCTCTGCACAACCACTACACGCAGAAGAGCCTCTCCCTGTCCCCGGGTAAAGG
ATCCGGG
```

Figure 3E

```
MALPVTALLLPLALLLHAARPENQMTQSPSSLSASVGDRVTMTCRASSSVSSSYLHWYQQKSGKAPKV
WIYSTSNLASGVPSRFSGSGSGTDYTLTISSLQPEDFATYYCQQYSGYPITFGQGTKVEIKGGGGSGG
GGSGGGGSQVQLQESGPGLVKPSQTLSITCTVSGFSLASYNIHWVRQPPGKGLEWLGVIWAGGSTNYN
SALMSRLTISKDNSKNQVFLKMSSLTAADTAVYYCAKRSDDYSWFAYWGQGTLVTVSSEPKSCDKTHT
CPPCPAPPVAGPSVFLFPPKPKDTLMIARTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVDKSRWQQGNVFSCSVMHE
ALHNHYTQKSLSLSPGKGF
```

Figure 3F

```
GGGGGATCCTTTTGGGTGCTGGTGGTGGTTGGTGGAGTCCTGGCTTGCTATAGCTTGCTAGTAACAGT
GGCCTTTATTATTTTCTGGGTGAGGAGTAAGAGGAGCAGGCTCCTGCACAGTGACTACATGAACATGA
CTCCCCGCCGCCCCGGGCCCACCCGCAAGCATTACCAGCCCTATGCCCCACCACGCGACTTCGCAGCC
TATCGCTCCAAACGGGGCAGAAAGAAACTCCTGTATATATTCAAACAACCATTTATGAGACCAGTACA
AACTACTCAAGAGGAAGATGGCTGTAGCTGCCGATTTCCAGAAGAAGAAGAAGGAGGATGTGAACTGA
GAGTGAAGTTCAGCAGGAGCGCAGACGCCCCCGCGTACCAGCAGGGCCAGAACCAGCTCTATAACGAG
CTCAATCTAGGACGAAGAGAGGAGTACGATGTTTTGGACAAGAGACGTGGCCGGGACCCTGAGATGGG
GGGAAAGCCGCAGAGAAGGAAGAACCCTCAGGAAGGCCTGTACAATGAACTGCAGAAAGATAAGATGG
CGGAGGCCTACAGTGAGATTGGGATGAAAGGCGAGCGCCGGAGGGGCAAGGGGCACGATGGCCTTTAC
CAGGGTCTCAGTACAGCCACCAAGGACACCTACGACGCCCTTCACATGCAGGCCCTGCCCCCTCGCTA
AGAATTCGGG
```

Figure 3G

```
FWVLVVVGGVLACYSLLVTVAFIIFWVRSKRSRLLHSDYMNMTPRRPGPTRKHYQPYAPPRDFAAYRS
KRGRKKLLYIFKQPFMRPVQTTQEEDGCSCRFPEEEEGGCELRVKFSRSADAPAYQQGQNQLYNELNL
GRREEYDVLDKRRGRDPEMGGKPQRRKNPQEGLYNELQKDKMAEAYSEIGMKGERRRGKGHDGLYQGL
STATKDTYDALHMQALPPR*   (* indicates stop codon)
```

Figure 3H

SEQUENCE LISTING

```
<160> NUMBER OF SEQ ID NOS: 28

<210> SEQ ID NO 1
<211> LENGTH: 1506
<212> TYPE: DNA
<213> ORGANISM: Artificial Sequence
<220> FEATURE:
<223> OTHER INFORMATION: construct for anti-ErbB2/HER2 receptor CAR
      based on antibody 4D5

<400> SEQUENCE: 1
gggaagcttg ccaccatggc cttaccagtg accgccttgc tcctgccgct ggccttgctg      60
ctccacgccg ccaggccgga tatccagatg acccagtccc cgagctccct gtccgcctct     120
gtgggcgata gggtcaccat cacctgccgt gccagtcagg atgtgaatac tgctgtagcc     180
```

```
tggtatcaac agaaaccagg aaaagctccg aaactactga tttactcggc atccttcctc      240
gagtctggag tcccttctcg cttctctggt tcgagatctg ggacggattt cactctgacc      300
atcagcagtc tgcagccgga agacttcgca acttattact gtcagcaaca ttatactact      360
cctcccacgt tcggacaggg taccaaggtg agatcaaag gtggtggtgg ttctggtggt       420
ggtggttctg gcggcggcgg ctccgaggtt cagctggtgg agtctggcgg tggcctggtg      480
cagccagggg gctcactccg tttgtcctgt gcagcttctg gcttcaacat taaagacacc      540
tatatacact gggtgcgtca ggccccgggt aagggcctgg aatgggttgc aaggatttat      600
cctacgaatg gttatactag atatgccgat agcgtcaagg gccgtttcac tataagcgca      660
gacacatcca aaacacagc ctacctgcag atgaacagcc tgcgtgctga ggacactgcc       720
gtctattatt gttctagatg gggaggggac ggcttctatg ctatggacgt gtggggtcaa      780
ggaaccctgg tcaccgtctc ctcggagccc aaatcttgtg acaaaactca cacatgccca      840
ccgtgcccag cacctccagt cgcgggaccg tcagtcttcc tcttcccccc aaaacccaag      900
gacaccctca tgatcgcccg acccctgag gtcacatgcg tggtggtgga cgtgagccac       960
gaagaccctg aggtcaagtt caactggtac gtggacggcg tggaggtgca taatgccaag     1020
acaaagccgc gggaggagca gtacaacagc acgtaccgtg tggtcagcgt cctcaccgtc     1080
ctgcaccagg actggctgaa tggcaaggag tacaagtgca aggtctccaa caaagccctc     1140
ccagccccca tcgagaaaac catctccaaa gccaagggc agccccgaga accacaggtg      1200
tacaccctgc cccatcccg ggaggagatg accaagaacc aggtcagcct gacctgcctg      1260
gtcaaaggct tctatcccag cgacatcgcc gtggagtggg agagcaatgg gcagccggag     1320
aacaactaca agaccacgcc tcccgtgctg gactccgacg gctccttctt cctctatagc     1380
aagctcaccg tggacaagag caggtggcag caggggaacg tcttctcatg ctccgtgatg     1440
catgaggctc tgcacaacca ctacacgcag aagagcctct ccctgtcccc gggtaaagga    1500
tccggg                                                                1506
```

<210> SEQ ID NO 2
<211> LENGTH: 496
<212> TYPE: PRT
<213> ORGANISM: Artificial Sequence
<220> FEATURE:
<223> OTHER INFORMATION: construct for anti-ErbB2/HER2 receptor CAR
      based on antibody 4D5

<400> SEQUENCE: 2

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Val Asn Thr Ala Val Ala Trp Tyr Gln Gln Lys Pro Gly Lys Ala
    50                  55                  60

Pro Lys Leu Leu Ile Tyr Ser Ala Ser Phe Leu Tyr Ser Gly Val Pro
65                  70                  75                  80

Ser Arg Phe Ser Gly Ser Arg Ser Gly Thr Asp Phe Thr Leu Thr Ile
                85                  90                  95

Ser Ser Leu Gln Pro Glu Asp Phe Ala Thr Tyr Tyr Cys Gln Gln His
            100                 105                 110

Tyr Thr Thr Pro Pro Thr Phe Gly Gln Gly Thr Lys Val Glu Ile Lys
```

```
                115              120               125
      Gly Gly Gly Gly Ser Gly Gly Gly Ser Gly Gly Gly Ser Glu
              130              135               140
      Val Gln Leu Val Glu Ser Gly Gly Leu Val Gln Pro Gly Gly Ser
      145                  150                155               160
      Leu Arg Leu Ser Cys Ala Ala Ser Gly Phe Asn Ile Lys Asp Thr Tyr
                        165                170                175
      Ile His Trp Val Arg Gln Ala Pro Gly Lys Gly Leu Glu Trp Val Ala
                    180                185                190
      Arg Ile Tyr Pro Thr Asn Gly Tyr Thr Arg Tyr Ala Asp Ser Val Lys
                    195                200                205
      Gly Arg Phe Thr Ile Ser Ala Asp Thr Ser Lys Asn Thr Ala Tyr Leu
              210                215                220
      Gln Met Asn Ser Leu Arg Ala Glu Asp Thr Ala Val Tyr Tyr Cys Ser
      225                  230                235                240
      Arg Trp Gly Gly Asp Gly Phe Tyr Ala Met Asp Val Trp Gly Gln Gly
                        245                250                255
      Thr Leu Val Thr Val Ser Ser Glu Pro Lys Ser Cys Asp Lys Thr His
                    260                265                270
      Thr Cys Pro Pro Cys Pro Ala Pro Pro Val Ala Gly Pro Ser Val Phe
                    275                280                285
      Leu Phe Pro Pro Lys Pro Lys Asp Thr Leu Met Ile Ala Arg Thr Pro
              290                295                300
      Glu Val Thr Cys Val Val Val Asp Val Ser His Glu Asp Pro Glu Val
      305                  310                315                320
      Lys Phe Asn Trp Tyr Val Asp Gly Val Glu Val His Asn Ala Lys Thr
                        325                330                335
      Lys Pro Arg Glu Glu Gln Tyr Asn Ser Thr Tyr Arg Val Val Ser Val
                    340                345                350
      Leu Thr Val Leu His Gln Asp Trp Leu Asn Gly Lys Glu Tyr Lys Cys
                    355                360                365
      Lys Val Ser Asn Lys Ala Leu Pro Ala Pro Ile Glu Lys Thr Ile Ser
              370                375                380
      Lys Ala Lys Gly Gln Pro Arg Glu Pro Gln Val Tyr Thr Leu Pro Pro
      385                  390                395                400
      Ser Arg Asp Glu Leu Thr Lys Asn Gln Val Ser Leu Thr Cys Leu Val
                        405                410                415
      Lys Gly Phe Tyr Pro Ser Asp Ile Ala Val Glu Trp Glu Ser Asn Gly
                    420                425                430
      Gln Pro Glu Asn Asn Tyr Lys Thr Thr Pro Pro Val Leu Asp Ser Asp
              435                440                445
      Gly Ser Phe Phe Leu Tyr Ser Lys Leu Thr Val Asp Lys Ser Arg Trp
              450                455                460
      Gln Gln Gly Asn Val Phe Ser Cys Ser Val Met His Glu Ala Leu His
      465                  470                475                480
      Asn His Tyr Thr Gln Lys Ser Leu Ser Leu Ser Pro Gly Lys Gly Phe
                        485                490                495

<210> SEQ ID NO 3
<211> LENGTH: 1554
<212> TYPE: DNA
<213> ORGANISM: Artificial Sequence
<220> FEATURE:
<223> OTHER INFORMATION: construct for anti-CD19 CAR based on mouse
      monoclonal antibody
```

<400> SEQUENCE: 3

```
gggaagcttg ccaccatggc cttaccagtg accgccttgc tcctgccgct ggccttgctg    60
ctccacgccg ccaggccgga catccagatg acacagacta catcctccct gtctgcctct   120
ctgggagaca gagtcaccat cagttgcagg gcaagtcagg acattagtaa atatttaaat   180
tggtatcagc agaaaccaga tggaactgtt aaactcctga tctaccatac atcaagatta   240
cactcaggag tcccatcaag gttcagtggc agtgggtctg gaacagatta ttctctcacc   300
attagcaacc tggagcaaga agatattgcc acttactttt gccaacaggg taatacgctt   360
ccgtacacgt tcggagggg gactaagttg gaaataacac gggctgatgc tgcaccaact   420
gtatccatct tcccaccatc cagtaatggt ggtggtggtt ctggtggtgg tggttctggc   480
ggcggcggct ccgaggtgaa actgcaggag tcaggacctg gcctggtggc gccctcacag   540
agcctgtccg tcacatgcac tgtctcaggg gtctcattac ccgactatgg tgtaagctgg   600
attcgccagc tccacgaaa gggtctggag tggctgggag taatatgggg tagtgaaacc   660
acatactata attcagctct caaatccaga ctgaccatca tcaaggacaa ctccaagagc   720
caagttttct aaaaatgaa cagtctgcaa actgatgaca cagccattta ctactgtgcc   780
aaacattatt actacggtgg tagctatgct atggactact ggggtcaagg aacctcagtc   840
accgtctcct cagagcccaa atcttgtgac aaaactcaca catgcccacc gtgcccagca   900
cctccagtcg cgggaccgtc agtcttcctc ttccccccaa aacccaagga caccctcatg   960
atcgcccgga cccctgaggt cacatgcgtg gtggtggacg tgagccacga agaccctgag  1020
gtcaagttca actggtacgt ggacggcgtg gaggtgcata atgccaagac aaagccgcgg  1080
gaggagcagt acaacagcac gtaccgtgtg gtcagcgtcc tcaccgtcct gcaccaggac  1140
tggctgaatg gcaaggagta caagtgcaag gtctccaaca aagcctccc agcccccatc  1200
gagaaaacca tctccaaagc caagggcag ccccgagaac acaggtgta caccctgccc  1260
ccatcccggg aggagatgac caagaaccag gtcagcctga cctgcctggt caaaggcttc  1320
tatcccagcg acatcgccgt ggagtgggag agcaatgggc agccggagaa caactacaag  1380
accacgcctc ccgtgctgga ctccgacggc tccttcttcc tctatagcaa gctcaccgtg  1440
gacaagagca ggtggcagca ggggaacgtc ttctcatgct ccgtgatgca tgaggctctg  1500
cacaaccact acacgcagaa gagcctctcc ctgtccccgg gtaaaggatc cggg         1554
```

<210> SEQ ID NO 4
<211> LENGTH: 512
<212> TYPE: PRT
<213> ORGANISM: Artificial Sequence
<220> FEATURE:
<223> OTHER INFORMATION: construct for anti-CD19 CAR based on mouse monoclonal antibody

<400> SEQUENCE: 4

```
Met Ala Leu Pro Val Thr Ala Leu Leu Leu Pro Leu Ala Leu Leu Leu
  1               5                  10                  15

His Ala Ala Arg Pro Asp Ile Gln Met Thr Gln Thr Thr Ser Ser Leu
             20                  25                  30

Ser Ala Ser Leu Gly Asp Arg Val Thr Ile Ser Cys Arg Ala Ser Gln
         35                  40                  45

Asp Ile Ser Lys Tyr Leu Asn Trp Tyr Gln Gln Lys Pro Asp Gly Thr
     50                  55                  60

Val Lys Leu Leu Ile Tyr His Thr Ser Arg Leu His Ser Gly Val Pro
```

```
                65                      70                      75                      80
            Ser Arg Phe Ser Gly Ser Gly Ser Gly Thr Asp Tyr Ser Leu Thr Ile
                                85                      90                      95
            Ser Asn Leu Glu Gln Glu Asp Ile Ala Thr Tyr Phe Cys Gln Gln Gly
                                100                     105                     110
            Asn Thr Leu Pro Tyr Thr Phe Gly Gly Gly Thr Lys Leu Glu Ile Thr
                                115                     120                     125
            Arg Ala Asp Ala Ala Pro Thr Val Ser Ile Phe Pro Pro Ser Ser Asn
                                130                     135                     140
            Gly Gly Gly Gly Ser Gly Gly Gly Ser Gly Gly Gly Gly Ser Glu
            145                     150                     155                     160
            Val Lys Leu Gln Glu Ser Gly Pro Gly Leu Val Ala Pro Ser Gln Ser
                                165                     170                     175
            Leu Ser Val Thr Cys Thr Val Ser Gly Val Ser Leu Pro Arg Tyr Gly
                                180                     185                     190
            Val Ser Trp Ile Arg Gln Pro Pro Arg Lys Gly Leu Glu Trp Leu Gly
                                195                     200                     205
            Val Ile Trp Gly Ser Glu Thr Thr Tyr Tyr Asn Ser Ala Leu Lys Ser
            210                     215                     220
            Arg Leu Thr Ile Ile Lys Asp Asn Ser Lys Ser Gln Val Phe Leu Lys
            225                     230                     235                     240
            Met Asn Ser Leu Gln Thr Asp Asp Thr Ala Ile Tyr Tyr Cys Ala Lys
                                245                     250                     255
            His Tyr Tyr Tyr Gly Gly Ser Tyr Ala Met Asp Tyr Trp Gly Gln Gly
                                260                     265                     270
            Thr Ser Val Thr Val Ser Ser Glu Pro Lys Ser Cys Asp Lys Thr His
                                275                     280                     285
            Thr Cys Pro Pro Cys Pro Ala Pro Pro Val Ala Gly Pro Ser Val Phe
                                290                     295                     300
            Leu Phe Pro Pro Lys Pro Lys Asp Thr Leu Met Ile Ala Arg Thr Pro
            305                     310                     315                     320
            Glu Val Thr Cys Val Val Val Asp Val Ser His Glu Asp Pro Glu Val
                                325                     330                     335
            Lys Phe Asn Trp Tyr Val Asp Gly Val Glu Val His Asn Ala Lys Thr
                                340                     345                     350
            Lys Pro Arg Glu Glu Gln Tyr Asn Ser Thr Tyr Arg Val Val Ser Val
                                355                     360                     365
            Leu Thr Val Leu His Gln Asp Trp Leu Asn Gly Lys Glu Tyr Lys Cys
                                370                     375                     380
            Lys Val Ser Asn Lys Ala Leu Pro Ala Pro Ile Glu Lys Thr Ile Ser
            385                     390                     395                     400
            Lys Ala Lys Gly Gln Pro Arg Glu Pro Gln Val Tyr Thr Leu Pro Pro
                                405                     410                     415
            Ser Arg Asp Glu Leu Thr Lys Asn Gln Val Ser Leu Thr Cys Leu Val
                                420                     425                     430
            Lys Gly Phe Tyr Pro Ser Asp Ile Ala Val Glu Trp Glu Ser Asn Gly
                                435                     440                     445
            Gln Pro Glu Asn Asn Tyr Lys Thr Thr Pro Pro Val Leu Asp Ser Asp
                                450                     455                     460
            Gly Ser Phe Phe Leu Tyr Ser Lys Leu Thr Val Asp Lys Ser Arg Trp
            465                     470                     475                     480
            Gln Gln Gly Asn Val Phe Ser Cys Ser Val Met His Glu Ala Leu His
                                485                     490                     495
```

Asn His Tyr Thr Gln Lys Ser Leu Ser Leu Ser Pro Gly Lys Gly Phe
                500                 505                 510

<210> SEQ ID NO 5
<211> LENGTH: 1503
<212> TYPE: DNA
<213> ORGANISM: Artificial Sequence
<220> FEATURE:
<223> OTHER INFORMATION: construct for anti-GD2 CAR based on antibody
      huKM666

<400> SEQUENCE: 5
gggaagcttg ccaccatggc cttaccagtg accgccttgc tcctgccgct ggccttgctg      60
ctccacgccg ccaggccgga gaaccagatg acccagagcc cagcagcct gagcgccagc      120 gtgggcgaca gagtgaccat gacctgcaga gccagcagca gcgtgagcag cagctacctg     180
cactggtacc agcagaagag cggcaaggcc cccaaggtgt ggatctacag caccagcaac     240
ctggccagcg gcgtgcccag cagattcagc ggcagcggca gcggcaccga ctacaccctg     300
accatcagca gcctgcagcc cgaggacttc gccacctact actgccagca gtacagcggc     360
taccccatca ccttcggcca gggcaccaag gtggagatca aggtggtgg tggttctggt      420 ggtggtggtt ctggcggcgg cggctcccag gtgcagctgc aggagagcgg ccccggcctg     480
gtgaagccca gccagaccct gagcatcacc tgcaccgtga cggcttcag cctggccagc      540 tacaacatcc actgggtgag acagccccc ggcaagggcc tggagtggct gggcgtgatc      600
tgggccggcg gcagcaccaa ctacaacagc gccctgatga gcagactgac catcagcaag     660
gacaacagca agaaccaggt gttcctgaag atgagcagcc tgaccgccgc cgacaccgcc     720
gtgtactact gcgccaagag aagcgacgac tacagctggt cgcctactg gggccagggc     780 accctggtga ccgtgagcag cgagcccaaa tcttgtgaca aaactcacac atgcccaccg     840
tgcccagcac ctccagtcgc gggaccgtca gtcttcctct ccccccaaa acccaaggac      900 accctcatga tcgcccggac ccctgaggtc acatgcgtgg tggtggacgt gagccacgaa     960
gaccctgagg tcaagttcaa ctggtacgtg gacggcgtgg aggtgcataa tgccaagaca    1020
aagccgcggg aggagcagta caacagcacg taccgtgtg tcagcgtcct caccgtcctg     1080
caccaggact ggctgaatgg caaggagtac aagtgcaagg tctccaacaa agccctccca    1140
gcccccatcg agaaaaccat ctccaaagcc aagggcagc cccgagaacc acaggtgtac     1200
accctgcccc catcccggga ggagatgacc aagaaccagg tcagcctgac ctgcctggtc    1260
aaaggcttct atcccagcga catcgccgtg gagtgggaga gcaatgggca gccggagaac    1320
aactacaaga ccacgcctcc cgtgctggac tccgacggct ccttcttcct ctatagcaag    1380
ctcaccgtgg acaagagcag gtggcagcag gggaacgtct tctcatgctc cgtgatgcat    1440
gaggctctgc acaaccacta cacgcagaag agcctctccc tgtccccggg taaaggatcc    1500
ggg                                                                  1503

<210> SEQ ID NO 6
<211> LENGTH: 495
<212> TYPE: PRT
<213> ORGANISM: Artificial Sequence
<220> FEATURE:
<223> OTHER INFORMATION: construct for anti-GD2 CAR based on antibody
      huKM666

<400> SEQUENCE: 6

Met Ala Leu Pro Val Thr Ala Leu Leu Leu Pro Leu Ala Leu Leu Leu

```
  1               5                   10                  15
His Ala Ala Arg Pro Glu Asn Gln Met Thr Gln Ser Pro Ser Ser Leu
            20                  25                  30

Ser Ala Ser Val Gly Asp Arg Val Thr Met Thr Cys Arg Ala Ser Ser
            35                  40                  45

Ser Val Ser Ser Ser Tyr Leu His Trp Tyr Gln Gln Lys Ser Gly Lys
 50                      55                  60

Ala Pro Lys Val Trp Ile Tyr Ser Thr Ser Asn Leu Ala Ser Gly Val
 65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Tyr Cys Gln Gln
                100                 105                 110

Tyr Ser Gly Tyr Pro Ile Thr Phe Gly Gln Gly Thr Lys Val Glu Ile
                115                 120                 125

Lys Gly Gly Gly Gly Ser Gly Gly Gly Gly Ser Gly Gly Gly Gly Ser
        130                 135                 140

Gln Val Gln Leu Gln Glu Ser Gly Pro Gly Leu Val Lys Pro Ser Gln
145                 150                 155                 160

Thr Leu Ser Ile Thr Cys Thr Val Ser Gly Phe Ser Leu Ala Ser Tyr
                165                 170                 175

Asn Ile His Trp Val Arg Gln Pro Pro Gly Lys Gly Leu Glu Trp Leu
                180                 185                 190

Gly Val Ile Trp Ala Gly Gly Ser Thr Asn Tyr Asn Ser Ala Leu Met
                195                 200                 205

Ser Arg Leu Thr Ile Ser Lys Asp Asn Ser Lys Asn Gln Val Phe Leu
        210                 215                 220

Lys Met Ser Ser Leu Thr Ala Ala Asp Thr Ala Val Tyr Tyr Cys Ala
225                 230                 235                 240

Lys Arg Ser Asp Asp Tyr Ser Trp Phe Ala Tyr Trp Gly Gln Gly Thr
                245                 250                 255

Leu Val Thr Val Ser Ser Glu Pro Lys Ser Cys Asp Lys Thr His Thr
                260                 265                 270

Cys Pro Pro Cys Pro Ala Pro Pro Val Ala Gly Pro Ser Val Phe Leu
                275                 280                 285

Phe Pro Pro Lys Pro Lys Asp Thr Leu Met Ile Ala Arg Thr Pro Glu
                290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
                340                 345                 350

Thr Val Leu His Gln Asp Trp Leu Asn Gly Lys Glu Tyr Lys Cys Lys
                355                 360                 365

Val Ser Asn Lys Ala Leu Pro Ala Pro Ile Glu Lys Thr Ile Ser Lys
        370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
                420                 425                 430
```

```
Pro Glu Asn Asn Tyr Lys Thr Thr Pro Pro Val Leu Asp Ser Asp Gly
            435                 440                 445

Ser Phe Phe Leu Tyr Ser Lys Leu Thr Val Asp Lys Ser Arg Trp Gln
        450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys Gly Phe
                485                 490                 495

<210> SEQ ID NO 7
<211> LENGTH: 690
<212> TYPE: DNA
<213> ORGANISM: Artificial Sequence
<220> FEATURE:
<223> OTHER INFORMATION: CD28-4-1 BB-CD3 zeta construct

<400> SEQUENCE: 7
gggggatcct tttgggtgct ggtggtggtt ggtggagtcc tggcttgcta tagcttgcta      60
gtaacagtgg cctttattat tttctgggtg aggagtaaga ggagcaggct cctgcacagt     120
gactacatga acatgactcc ccgccgcccc gggcccaccc gcaagcatta ccagccctat     180
gccccaccac gcgacttcgc agcctatcgc tccaaacggg gcagaaagaa actcctgtat     240
atattcaaac aaccatttat gagaccagta caaactactc aagaggaaga tggctgtagc     300
tgccgatttc cagaagaaga agaaggagga tgtgaactga gagtgaagtt cagcaggagc     360
gcagacgccc ccgcgtacca gcagggccag aaccagctct ataacgagct caatctagga     420
cgaagagagg agtacgatgt tttggacaag agacgtggcc gggaccctga gatgggggga     480
aagccgcaga gaaggaagaa ccctcaggaa ggcctgtaca atgaactgca gaaagataag     540
atggcggagg cctacagtga gattgggatg aaaggcgagc gccggagggg caaggggcac     600
gatggccttt accagggtct cagtacagcc accaaggaca cctacgacgc ccttcacatg     660
caggccctgc ccctcgcta agaattcggg                                        690

<210> SEQ ID NO 8
<211> LENGTH: 223
<212> TYPE: PRT
<213> ORGANISM: Artificial Sequence
<220> FEATURE:
<223> OTHER INFORMATION: CD28-4-1 BB-CD3 zeta construct

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser Lys Arg Gly Arg Lys Lys Leu Leu Tyr Ile Phe Lys
65                  70                  75                  80

Gln Pro Phe Met Arg Pro Val Gln Thr Thr Gln Glu Glu Asp Gly Cys
                85                  90                  95

Ser Cys Arg Phe Pro Glu Glu Glu Glu Gly Gly Cys Glu Leu Arg Val
            100                 105                 110

Lys Phe Ser Arg Ser Ala Asp Ala Pro Ala Tyr Gln Gln Gly Gln Asn
```

|  | 115 |  | 120 |  | 125 |  |  |
|--|--|--|--|--|--|--|--|

Gln Leu Tyr Asn Glu Leu Asn Leu Gly Arg Arg Glu Glu Tyr Asp Val
130                 135                 140

Leu Asp Lys Arg Arg Gly Arg Asp Pro Glu Met Gly Gly Lys Pro Gln
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
            180                 185                 190

Arg Gly Lys Gly His Asp Gly Leu Tyr Gln Gly Leu Ser Thr Ala Thr
        195                 200                 205

Lys Asp Thr Tyr Asp Ala Leu His Met Gln Ala Leu Pro Pro Arg
    210                 215                 220

<210> SEQ ID NO 9
<211> LENGTH: 141
<212> TYPE: DNA
<213> ORGANISM: Artificial Sequence
<220> FEATURE:
<223> OTHER INFORMATION: CBL shRNA

<400> SEQUENCE: 9
gaaggctcga gaaggtatat tgctgttgac agtgagcgaa gcagctagta tgttttatta      60
tagtgaagcc acagatgtat aataaaacat actagctgct ctgcctactg cctcggactt     120
caaggggcta gaattcgagc a                                               141

<210> SEQ ID NO 10
<211> LENGTH: 141
<212> TYPE: DNA
<213> ORGANISM: Artificial Sequence
<220> FEATURE:
<223> OTHER INFORMATION: CBL shRNA

<400> SEQUENCE: 10
gaaggctcga gaaggtatat tgctgttgac agtgagcgct cagtggttcc aagatttcaa      60
tagtgaagcc acagatgtat tgaaatcttg gaaccactga ttgcctactg cctcggactt     120
caaggggcta gaattcgagc a                                               141

<210> SEQ ID NO 11
<211> LENGTH: 22
<212> TYPE: DNA
<213> ORGANISM: Artificial Sequence
<220> FEATURE:
<223> OTHER INFORMATION: CBL shRNA target

<400> SEQUENCE: 11
agcagctagt atgttttatt at                                              22

<210> SEQ ID NO 12
<211> LENGTH: 21
<212> TYPE: DNA
<213> ORGANISM: Artificial Sequence
<220> FEATURE:
<223> OTHER INFORMATION: CBL shRNA target

<400> SEQUENCE: 12
tcagtggttc caagatttca a                                               21

<210> SEQ ID NO 13
<211> LENGTH: 19

```
<212> TYPE: DNA
<213> ORGANISM: Artificial Sequence
<220> FEATURE:
<223> OTHER INFORMATION: CBL shRNA target

<400> SEQUENCE: 13
ggcgaaacct aaccaaact                                                     19

<210> SEQ ID NO 14
<211> LENGTH: 141
<212> TYPE: DNA
<213> ORGANISM: Artificial Sequence
<220> FEATURE:
<223> OTHER INFORMATION: CBL-B shRNA

<400> SEQUENCE: 14
gaaggctcga gaaggtatat tgctgttgac agtgagcgat cagtgagaat gagtacttta        60
tagtgaagcc acagatgtat aaagtactca ttctcactga gtgcctactg cctcggactt       120
caagggctca gaattcgagc a                                                 141

<210> SEQ ID NO 15
<211> LENGTH: 141
<212> TYPE: DNA
<213> ORGANISM: Artificial Sequence
<220> FEATURE:
<223> OTHER INFORMATION: CBL-B shRNA

<400> SEQUENCE: 15
gaaggctcga gaaggtatat tgctgttgac agtgagcgaa ggtgaaaatg tcaaaactaa        60
tagtgaagcc acagatgtat tagttttgac attttcacct gtgcctactg cctcggactt       120
caagggctca gaattcgagc a                                                 141

<210> SEQ ID NO 16
<211> LENGTH: 21
<212> TYPE: DNA
<213> ORGANISM: Artificial Sequence
<220> FEATURE:
<223> OTHER INFORMATION: CBL-B shRNA target

<400> SEQUENCE: 16
aggtgaaaat gtcaaaacta a                                                  21

<210> SEQ ID NO 17
<211> LENGTH: 20
<212> TYPE: DNA
<213> ORGANISM: Artificial Sequence
<220> FEATURE:
<223> OTHER INFORMATION: CBL-B shRNA target

<400> SEQUENCE: 17
cagtgagaat gagtacttta                                                    20

<210> SEQ ID NO 18
<211> LENGTH: 19
<212> TYPE: DNA
<213> ORGANISM: Artificial Sequence
<220> FEATURE:
<223> OTHER INFORMATION: CBL-B shRNA target

<400> SEQUENCE: 18
gaccatacct cataacaag                                                     19

<210> SEQ ID NO 19
```

```
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 19

Pro Glu Leu Leu Gly Gly
1               5

<210> SEQ ID NO 20
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 20
cctgaactcc tgggggga                                                     18

<210> SEQ ID NO 21
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 21

Pro Pro Val Ala Gly
1               5

<210> SEQ ID NO 22
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 22
cctccagtcg cggga                                                        15

<210> SEQ ID NO 23
<211> LENGTH: 141
<212> TYPE: DNA
<213> ORGANISM: Artificial Sequence
<220> FEATURE:
<223> OTHER INFORMATION: CBL shRNA

<400> SEQUENCE: 23
gaaggctcga gaaggtatat tgctgttgac agtgagcgcc agacaatcc ctcacaataa        60 tagtgaagcc acagatgtat tattgtgagg gattgtctgg atgcctactg cctcggactt      120
caaggggcta gaattcgagc a                                                141

<210> SEQ ID NO 24
<211> LENGTH: 141
<212> TYPE: DNA
<213> ORGANISM: Artificial Sequence
<220> FEATURE:
<223> OTHER INFORMATION: CBL shRNA

<400> SEQUENCE: 24
gaaggctcga gaaggtatat tgctgttgac agtgagcgct ccatctactg tggtattata       60
tagtgaagcc acagatgtat ataataccac agtagatgga atgcctactg cctcggactt      120
caaggggcta gaattcgagc a                                                141
```

```
<210> SEQ ID NO 25
<211> LENGTH: 141
<212> TYPE: DNA
<213> ORGANISM: Artificial Sequence
<220> FEATURE:
<223> OTHER INFORMATION: CBL shRNA

<400> SEQUENCE: 25
gaaggctcga gaaggtatat tgctgttgac agtgagcgac caggtatgtg ttctgatgta      60
tagtgaagcc acagatgtat acatcagaac acatacctgg ctgcctactg cctcggactt     120 caagggcta gaattcgagc a                                                 141

<210> SEQ ID NO 26
<211> LENGTH: 141
<212> TYPE: DNA
<213> ORGANISM: Artificial Sequence
<220> FEATURE:
<223> OTHER INFORMATION: CBL-B shRNA

<400> SEQUENCE: 26
gaaggctcga gaaggtatat tgctgttgac agtgagcgcc cagaaattca ccacagaaaa      60
tagtgaagcc acagatgtat tttctgtggt gaatttctgg ttgcctactg cctcggactt     120 caagggcta gaattcgagc a                                                 141

<210> SEQ ID NO 27
<211> LENGTH: 141
<212> TYPE: DNA
<213> ORGANISM: Artificial Sequence
<220> FEATURE:
<223> OTHER INFORMATION: CBL-B shRNA

<400> SEQUENCE: 27
gaaggctcga gaaggtatat tgctgttgac agtgagcgac cagaactgta gacaccaaaa      60
tagtgaagcc acagatgtat tttggtgtct acagttctgg ctgcctactg cctcggactt     120 caagggcta gaattcgagc a                                                 141

<210> SEQ ID NO 28
<211> LENGTH: 10
<212> TYPE: DNA
<213> ORGANISM: Artificial Sequence
<220> FEATURE:
<223> OTHER INFORMATION: Synthetic sequence

<400> SEQUENCE: 28
gccaccatgg                                                              10
```

CAR T-CELLS COMPRISING INACTIVATED CBL AND CBL-B GENES

This application is a § 371 application of PCT/US2018/019408, filed Feb. 23, 2018, which claims priority under 35 U.S.C. § 119 (e) to U.S. Provisional Patent Application No. 62/462,641, filed on Feb. 23, 2017 and U.S. Provisional Patent Application No. 62/473,802, filed on Mar. 20, 2017. The foregoing applications are incorporated by reference herein.

This invention was made with government support under Grant No. R01 CA099163, R01 CA087986, R01 CA105489, and R01 CA116552 awarded by the National Institutes of Health. The government has certain rights in the invention.

FIELD OF THE INVENTION

The present invention relates to the field of cancer. More specifically, the invention provides compositions and methods for the treatment of cancer.

BACKGROUND OF THE INVENTION

Several publications and patent documents are cited throughout the specification in order to describe the state of the art to which this invention pertains. Each of these citations is incorporated herein by reference as though set forth in full.

Chimeric antigen receptors (CARs) comprise the antigen-binding region of an antibody directed against a surface antigen selectively/specifically expressed on the tumor/cancer cell surface that is fused to the signaling elements of T-cell Receptor (TCR)-associated chain (e.g., first generation CAR). Additional signaling elements from T-cell co-receptors such as CD28 or 4-1BB (second generation CAR) or both (third generation CAR) may be used. Introduction of CARs into patient-derived cytotoxic T cells generates CAR-T cells that upon infusion back into a patient exhibit significant and selective killing of the tumor or cancer cells against which their CAR cells are targeted. Initial clinical experience has shown significant activity of CAR-T cells in hematological malignancies, such as the treatment of B-cell leukemia with CD19-directed CAR-T cells. Indeed, clinical trials on CAR-modified T cells for adults and pediatric patients with B cell malignancies have been reported (e.g., Porter et al. (2011) N. Engl. J. Med., 365:725-33; Grupp et al. (2013) N. Engl. J. Med., 368:1509-18). CAR-T cells have now been generated against a variety of antigens, but their efficacy against solid tumors, while promising, has proven to be more modest. Key reasons for poor efficacy of CAR-T cells include their inefficient traffic to tumor sites, ineffective tumor killing due to low cytotoxic activity as result of immune tolerance development and exhaustion because of altered immune microenvironment of tumors. Improved methods for using CAR-T technology, particularly against solid tumors, are needed.

SUMMARY OF THE INVENTION

In accordance with one aspect of the instant invention, compositions and methods for improving the efficacy of a chimeric antigen receptor T-cell (CAR-T) therapy are provided. In a particular embodiment, the methods comprise inhibiting and/or reducing the expression of CBL and/or CBL-B in the chimeric antigen receptor T-cells prior to administration of the T cells to a subject. In a particular embodiment, CBL and/or CBL-B expression is reduced through the use of an inhibitory nucleic acid molecule such as siRNA or shRNA. In a particular embodiment, CBL and/or CBL-B expression is reduced through the deletion or inactivation of the CBL and/or CBL-B genes (e.g., by CRISPR editing).

In accordance with another aspect of the instant invention, compositions and methods of treating and/or inhibiting cancer in a subject are provided. In a particular embodiment, the method comprises administering T cells that express i) a chimeric antigen receptor specific for the cancer to be treated and ii) at least one inhibitory nucleic acid molecule (e.g., siRNA or shRNA) for CBL and/or CBL-B. In a particular embodiment, the cancer is a solid tumor. In a particular embodiment, the cancer is a hematological tumor. In a particular embodiment, the T cells are autologous to the patient being treated.

In accordance with another aspect of the instant invention, vectors comprising i) a nucleic acid sequence encoding a chimeric antigen receptor and ii) a nucleic acid sequence encoding at least one inhibitory nucleic acid molecule for CBL and/or CBL-B are provided. Additionally, isolated T cells comprising a nucleic acid molecule encoding a chimeric antigen receptor and at least one inhibitory nucleic acid molecule for CBL or CBL-B are also provided. Compositions comprising the vectors or T cells of the instant invention and at least one carrier are also provided.

BRIEF DESCRIPTION OF THE DRAWINGS

FIG. 3A provides a DNA sequence (SEQ ID NO: 1) of a construct for anti-ErbB2/HER2 receptor CAR based on antibody 4D5. T and G residues were substituted for A and C to eliminate internal BamHI site without affecting the coded amino acid sequence. FIG. 3B provides an amino acid sequence (SEQ ID NO: 2) of this construct for anti-ErbB2/HER2 receptor CAR based on antibody 4D5. C-terminal GF amino acid residues are from the restriction enzyme site. FIG. 3C provides a DNA sequence (SEQ ID NO: 3) of a construct for anti-CD19 CAR based on a mouse monoclonal anti-CD19 antibody. FIG. 3D provides an amino acid sequence (SEQ ID NO: 4) of this construct for anti-CD19 CAR. C-terminal GF is from the restriction enzyme site. FIG. 3E provides a DNA sequence (SEQ ID NO: 5) of a construct for anti-GD2 CAR based on a mouse monoclonal anti-GD2 antibody huKM666. FIG. 3F provides an amino acid sequence (SEQ ID NO: 6) of this construct for anti-GD2 CAR. C-terminal GF amino acid residues are from the restriction enzyme site. FIG. 3G provides a DNA sequence (SEQ ID NO: 7) of a CD28-4-1BB-CD3 zeta construct. The 5' and 3' GGG sequences are G clamps to facilitate restriction enzyme cleavage for directional cloning. FIG. 3H provides an amino acid sequence (SEQ ID NO: 8) of this construct.

DETAILED DESCRIPTION OF THE INVENTION

Figure 1:
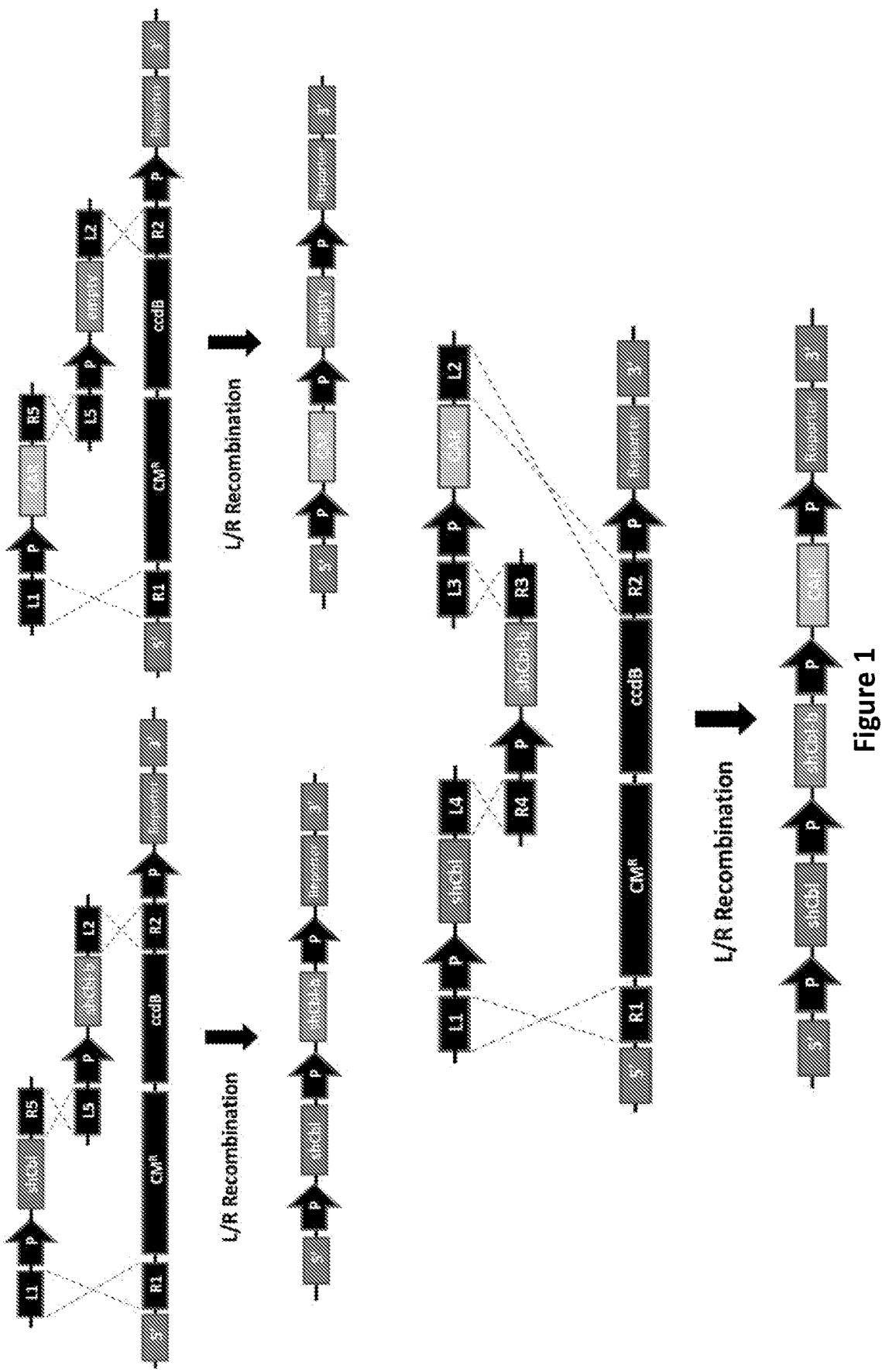
FIG. 1 provides a schematic of the assembly of shRNA elements against Cbl (shCbl) and Cbl-b (shCbl-b) together with a chimeric antigen receptor (CAR) to derive a Hyper-CAR expression construct with a reporter for selection of T-cells successfully transduced after lentiviral-mediated infection.

Members of the CBL family (CBL, CBL-B and CBL-C in mammals) of ubiquitin ligases serve as negative regulators of protein tyrosine kinases (PTKs), including receptor tyrosine kinases (RTKs) and non-receptor PTKs (Mohapatra et al. (2013) Biochim. Biophys. Acta 1833:122-139). Key physiological roles of CBL and CBL-B, individually as well as in combination, have been identified, especially as negative regulators of immune responses and hematopoiesis (An et al. (2015) Oncotarget 6:10498-10509; Duan et al. (2004) Immunity 21:7-17; Naramura et al. (2010) Proc. Natl. Acad. Sci., 107:16274-16279; Thien et al. (2005) Biochem J. 391:153-166; Mohapatra et al. (2013) Biochim. Biophys. Acta 1833:122-139). Notably, germline Cbl and Cbl-b double knockout mice (Cbl/Cbl-b DKO) are embryonic lethal (Naramura et al. (2002) Nat. Immunol., 3:1192-1199). Conditional CBL deletion in immune cells Cbl-nice mice results in an exaggeration of immune phenotypes (Kitaura et al. (2007) Immunity 26:567-578; Naramura et al. (2002) Nat. Immunol., 3:1192-1199).

CBL and CBL-B are expressed in T cells. Individual deletion of mouse CBL or CBL-B genes revealed their primary roles in developing and mature T cells, respectively. While deletion of the CBL gene led to altered thymocyte development (Naramura, et al. (1998) Proc. Natl. Acad. Sci., 95:15547-15552), Cbl-b deletion led to hyperactivity of mature T cells to antigenic stimulation (Chiang et al. (2000) Nature 403:216-220). CBL-B-null T cells can be activated by TCR engagement alone (without CD28 co-stimulation), are hyperactive to TCR plus CD28 stimulation, and show resistance to induction of an anergic state (Chiang, et al. (2000) Nature 403:216-220; Bachmaier, et al. (2000) Nature 403:211-216; Heissmeyer, et al. (2004) Nat. Immunol. 5:255-265). Cbl-b-null mice reject spontaneous and implanted tumors (Chiang, et al. (2007) J. Clin. Invest. 117:1029-1036; Loeser, et al. (2007) J. Exp. Med., 204:879-891). Depletion of CBL-B in human CD8+ T cells enhances their cytotoxic activity and promotes their tumor cell-killing ability (Lutz-Nicoladoni, et al. (2012) Immunol. Cell Biol. 90:130-134). However, when CBL gene is selectively deleted in T cells of whole-body CBL-B knockout mice, T-cells are markedly more hyper-active, traffic to organ sites and produce inflammatory disease (Naramura, et al. (2002) Nat. Immunol. 3:1192-119). Using a fully conditional model of CBL and CBL-B deficiency, concurrent deletion of CBL and CBL-B also leads to dramatically more hyper-active T cells (Goetz, et al. (2016) Oncotarget 7:51107-51123). These results support a redundant role of CBL and CBL-B in limiting T cell activation.

The CBL and/or CBL-B depleted CAR-T cells exhibit several advantages over unmodified CAR T-cells. Without being bound by theory, the CBL and/or CBL-B depleted CAR-T cells, once infused back into the cancer patient, more easily exit the circulation and reach tumor sites, aided by the selective homing properties of the CAR, thereby increasing the proportion of CAR-T cells that traffic to tumors. Once in the tumor, the inability of CBL and/or CBL-B depleted CAR-T cells to be tolerized by the immune microenvironment of tumors leads to more robust and sustained tumor cell killing. Further, given the hyper-active phenotype of the CBL and/or CBL-B depleted CAR-T cells, a smaller number of these cells are needed for anti-tumor activity in a patient, thereby limiting potential toxicity. Finally, as explained hereinbelow, the CBL and/or CBL-B depleted CAR-T cells enhance and speed up production of CAR-T therapy through faster in vitro CAR-T cell expansion from a smaller number of initial patient-derived T cells, reducing time and cost or production.

In accordance with the instant invention, compositions and methods to deplete and/or inhibit CBL and/or CBL-B (e.g., deplete and/or inhibit their expression) are provided. Amino acid and nucleotide sequences for CBL are available at Gene ID: 867 and GenBank Accession Nos. NM_005188.3 and NP 005179.2. Amino acid and nucleotide sequences for CBL-B are available at Gene ID: 868 and GenBank Accession Nos. NM_001321786.1 and NP 001308715.1. In a particular embodiment, CBL and/or CBL-B are inhibited in CAR-T cells. For example, CBL and/or CBL-B may be inhibited and the expression of CAR may be induced in cytotoxic T-cells. CAR-T cells wherein CBL and/or CBL-B are inhibited and/or reduced (typically when both are reduced or inhibited) are sometimes referred to herein as Hyper-active CAR-T cells (Hyper-CAR-T). Hyper-CAR-T cells are more active and provide more efficacious results compared to normal CAR-T therapy. In a particular embodiment, only CBL is inhibited or reduced (e.g., its expression in CAR-T cells is decreased). In a particular embodiment, only CBL-B is inhibited or reduced (e.g., its expression in CAR-T cells is decreased). In a particular embodiment, both CBL and CBL-B are inhibited or reduced (e.g., their expression in CAR-T cells is decreased). It is also envisioned that the compositions and methods of the present invention modulate the expression of other genes in combination with CBL and/or CBL-B.

CBL and/or CBL-B may be inhibited or reduced by any known means (e.g., small molecule inhibitors, blocking antibodies, inhibitory nucleic acid molecules). In a particular embodiment, CBL and/or CBL-B are inhibited or reduced by inhibitory nucleic acid molecules (e.g., antisense, siRNA, shRNA, miRNA, etc.). Examples for reducing and/or depleting the expression of CBL and/or CBL-B include, but are not limited to: siRNA specific for CBL and/or CBL-B, shRNA specific for CBL and/or CBL-B, and miRNA specific for CBL and/or CBL-B. In a particular embodiment, CBL and/or CBL-B are inhibited or reduced by using CBL and/or CBL-B specific CRISPR (clustered regularly interspaced short palindromic repeats) or CBL and/or CBL-B specific TALEN (transcription activator-like effector nucleases). In a particular embodiment, shRNA or siRNA specific for CBL and CBL-B are used.

Examples of CBL shRNA include:

```
                                            (SEQ ID NO: 9)
GAAGGCTCGAGAAGGTATATTGCTGTTGACAGTGAGCGAAGCAGCTAGTA

TGTTTTATTATAGTGAAGCCACAGATGTATAATAAAACATACTAGCTGCT

CTGCCTACTGCCTCGGACTTCAAGGGGCTAGAATTCGAGCA,
```

-continued (SEQ ID NO: 10)
GAAGGCTCGAGAAGGTATATTGCTGTTGACAGTGAGCGCTCAGTGGTTCC

AAGATTTCAATAGTGAAGCCACAGATGTATTGAAATCTTGGAACCACTGA

TTGCCTACTGCCTCGGACTTCAAGGGGCTAGAATTCGAGCA;

(SEQ ID NO: 23)
GAAGGCTCGAGAAGGTATATTGCTGTTGACAGTGAGCGCCCAGACAATCC

CTCACAATAATAGTGAAGCCACAGATGTATTATTGTGAGGGATTGTCTGG

ATGCCTACTGCCTCGGACTTCAAGGGGCTAGAATTCGAGCA;

(SEQ ID NO: 24)
GAAGGCTCGAGAAGGTATATTGCTGTTGACAGTGAGCGCTCCATCTACTG

TGGTATTATATAGTGAAGCCACAGATGTATATAATACCACAGTAGATGGA

ATGCCTACTGCCTCGGACTTCAAGGGGCTAGAATTCGAGCA;
and (SEQ ID NO: 25)
GAAGGCTCGAGAAGGTATATTGCTGTTGACAGTGAGCGACCAGGTATGTG

TTCTGATGTATAGTGAAGCCACAGATGTATACATCAGAACACATACCTGG

CTGCCTACTGCCTCGGACTTCAAGGGGCTAGAATTCGAGCA.

Figure 4:
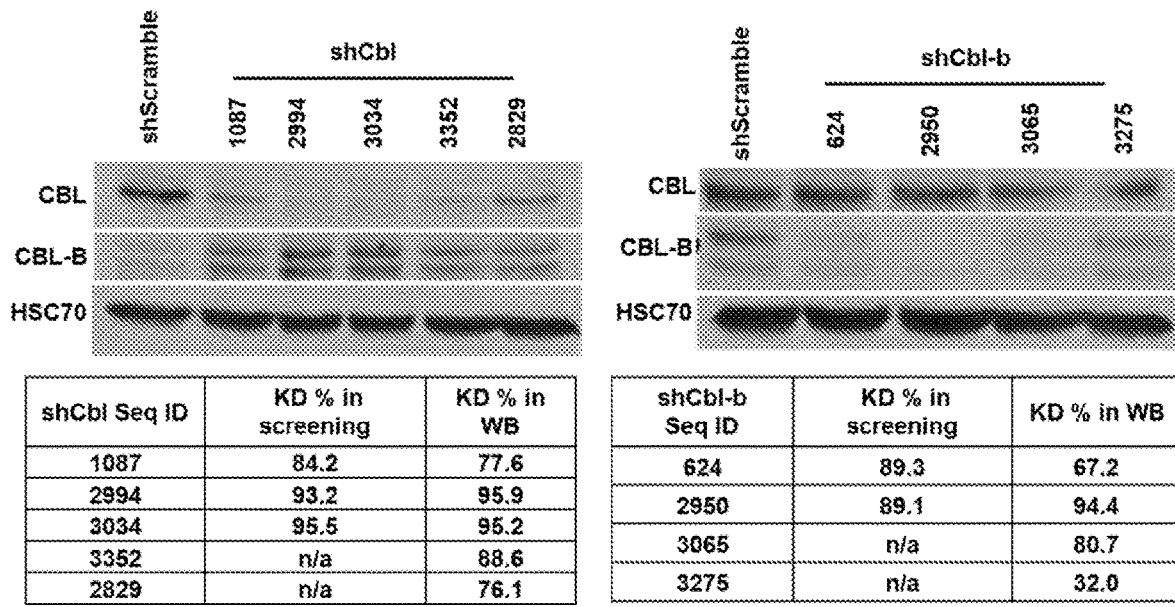
FIG. 4 demonstrates the knockdown efficiency (KD %) of shRNA sequences targeting CBL or CBL-B identified through sensor-based screening and verified upon stable retroviral expression in HEK-293T cells using Western blotting (WB). Densitometric quantification is shown in last column of tables below. Higher CBL-B signals with efficient CBL shRNAs may be due to compensation. The reverse was not seen. n/a: not available. Cbl_3034 is SEQ ID NO: 9; Cbl_2994 is SEQ ID NO: 10; Cbl_1087 is SEQ ID NO: 23; Cbl_3352 is SEQ ID NO: 24; Cbl_2829 is SEQ ID NO: 25; Cbl-b_624 is SEQ ID NO: 14; Cbl-b_2950 is SEQ ID NO: 15; Cbl-b_3065 is SEQ ID NO: 26; and Cbl-b_3275 is SEQ ID NO: 27.

Underlined sequences comprise target sequences within CBL and form the mature siRNA. These shRNA were tested for knockdown efficiency relative to a positive control (Ren 713 for *Renilla* luciferase) using a fluorescent-based reporter assay (Fellman et al. (2013) Cell Reports 5:1-10). SEQ ID NO: 9 resulted in a 95% knockdown and SEQ ID NO: 10 resulted in a 93% knockdown. These sequences were also stably expressed using a retrovirus construct in the human embryonic kidney epithelial cell line HEK-293T and specific knockdown of CBL—but not CBL-B—was confirmed by Western blot (FIG. 4). In a particular embodiment, the CBL inhibitory nucleic acid molecules (e.g., siRNA or shRNA) target and/or encompass the target sequence of SEQ ID NO: 9, 10, 23, 24, or 25. In a particular embodiment, the CBL inhibitory nucleic acid molecules (e.g., siRNA or shRNA) target and/or encompass AGCAGCTAGTATGTTTTATTAT (SEQ ID NO: 11), TCAGTGGTTCCAAGATTTCAA (SEQ ID NO: 12), or GGCGAAACCTAACCAAACT (SEQ ID NO: 13; Duan et al. (2011) J. Biol. Chem., 286:620-633).

Examples of CBL-B shRNA include:

(SEQ ID NO: 14)
GAAGGCTCGAGAAGGTATATTGCTGTTGACAGTGAGCGATCAGTGAGAAT

GAGTACTTTATAGTGAAGCCACAGATGTATAAAGTACTCATTCTCACTGA

GTGCCTACTGCCTCGGACTTCAAGGGGCTAGAATTCGAGCA;

(SEQ ID NO: 15)
GAAGGCTCGAGAAGGTATATTGCTGTTGACAGTGAGCGAAGGTGAAAATG

TCAAAACTAATAGTGAAGCCACAGATGTATTAGTTTTGACATTTTCACCTG

TGCCTACTGCCTCGGACTTCAAGGGGCTAGAATTCGAGCA;

(SEQ ID NO: 26)
GAAGGCTCGAGAAGGTATATTGCTGTTGACAGTGAGCGCCCAGAAATTCA

CCACAGAAATAGTGAAGCCACAGATGTATTTTCTGTGGTGAATTTCTGGT

TGCCTACTGCCTCGGACTTCAAGGGGCTAGAATTCGAGCA;
and (SEQ ID NO: 27)
GAAGGCTCGAGAAGGTATATTGCTGTTGACAGTGAGCGACCAGAACTGTA

GACACCAAAATAGTGAAGCCACAGATGTATTTTGGTGTCTACAGTTCTGG

CTGCCTACTGCCTCGGACTTCAAGGGGCTAGAATTCGAGCA.

Underlined sequences comprise target sequences within CBL-B and form the mature siRNA. These shRNA were tested for knockdown efficiency relative to a positive control (Ren 713 for *Renilla* luciferase) using a fluorescent-based reporter assay (Fellman et al. (2013) Cell Reports 5:1-10). SEQ ID NO: 14 resulted in a 89% knockdown and SEQ ID NO: 15 resulted in a 89% knockdown. These sequences were also stably expressed using a retrovirus construct in the human embryonic kidney epithelial cell line HEK-293T and specific knockdown of CBL-B—but not CBL—was confirmed by Western blot (see FIG. 4). In a particular embodiment, the CBL-B inhibitory nucleic acid molecules (e.g., siRNA or shRNA) target and/or encompass the target sequences within SEQ ID NO: 14, 15, 26, or 27. In a particular embodiment, the CBL-B inhibitory nucleic acid molecules (e.g., siRNA or shRNA) target and/or encompass AGGTGAAAATGTCAAAACTAA (SEQ ID NO: 16), CAGTGAGAATGAGTACTTTA (SEQ ID NO: 17), or GACCATACCTCATAACAAG (SEQ ID NO: 18; Duan et al. (2011) J. Biol. Chem., 286:620-633).

CBL and CBL-B depletion/knockdown can be used with any CAR. The CAR can target or specifically bind any tumor or cancer cell surface antigen. Examples of CARs that can be used in the instant invention include, without limitation: anti-CD19, anti-HER2, anti-CD20, anti-CD22, anti-CD171, anti-CD33, anti-CD123, anti-CD133, anti-CD138, anti-CD30, anti-EGFR, anti-EGFR variant III, anti-mesothelin, anti-prostate specific membrane antigen, anti-FGFR, anti-ErbB, anti-ErbB2, anti-kappa light chain, anti-VEGFR, anti-NKG2D, anti-glypican 3 (GPC3), anti-fibroblast activation protein, anti-cancer/testis antigen 1B (CTAG1B), anti-alpha V Beta 6 Integrin, anti-Lewis-Y, anti-WT-1, anti-ROR1, anti-MUC16, anti-MUC1, anti-MUC4, anti-GD2, anti-alpha folate receptor, anti-CAIX, anti-carcinoembryonic antigen (CEA), and anti-IL13Rα directed CARs.

Typically, chimeric antigen receptor-modified T cells express an antibody (e.g., a single chain Fv region of a monoclonal antibody) to recognize a cell-surface antigen independent of the major histocompatibility complex (MHC) coupled with one or more signaling molecules to activate genetically modified T cells for killing, proliferation, and cytokine production. Compositions and methods for CAR-T therapy are described, for example, in U.S. Pat. Nos. 9,821,012; 9,815,901; 9,777,061; 9,394,368; 9,328,156; 9,855,298; 7,446,190; 7,638,325; and 8,399,645, all of which are incorporated by reference herein.

Generally, the chimeric antigen receptor comprises an ectodomain (extracellular domain), a transmembrane domain, and an endodomain (cytoplasmic or intracellular domain). The ectodomain of the chimeric antigen receptor typically comprises an antibody or fragment thereof which is immunologically specific for the extracellular domain of the target molecule (e.g., a tumor or cancer cell surface antigen). The antibody or an antigen-binding fragment of the ectodomain may be linked to the transmembrane domain via an amino acid linker/spacer and may also comprise a signal peptide (e.g., an endoplasmic reticulum signal peptide (e.g., the signal peptide sequence from CD8, particularly CD8 alpha)).

The transmembrane domain of the chimeric antigen receptor may be any transmembrane domain. Generally, the transmembrane domain is a hydrophobic alpha helix that spans the cell membrane and is often from the same protein as the endodomain. Examples of transmembrane domains include, without limitation, transmembrane domains from T-cell receptor (TCR), CD28, CD3 (CD3-ζ), CD45, CD4, CD5, CD8, CD9, CD16, CD22, CD33, CD37, CD64, CD80, CD86, CD134, CD137, or CD154. In a particular embodiment, the transmembrane domain is from CD28.

The endodomain of a chimeric antigen receptor comprises at least one signaling domain (e.g., a signaling domain comprising one or more immunoreceptor tyrosine-based activation motifs (ITAMs)). The signaling domain is activated by antigen binding to the ectodomain and leads to the activation of the T cells. Signaling domains include, without limitation, the signaling domain (e.g., endodomain/cytoplasmic domain or fragment thereof) from CD3 (e.g., CD3-ε, CD3-γ, or CD3-ζ), LIGHT, lymphocyte function-associated antigen 1 (LFA-1), CD2, CD28, ICOS, CD30, CD7, NKG2C, CD40, PD-1, OX40, CD18, CD27, B7-H3, and 4-1BB. In a particular embodiment, the endodomain comprises more than one signaling domain. In a particular embodiment, the endodomain comprises CD28 and 4-1BB. In a particular embodiment, the endodomain comprises CD3-ζ, CD28, and 4-1BB.

Several CAR constructs are described in the Example hereinbelow. In a particular embodiment of the invention, the CAR comprises the CD8 signal peptide, an scFv, human IgG1 (e.g., the modified IgG1 described hereinbelow), the human CD28 transmembrane domain, and the signaling domains from CD3-ζ, CD28, and/or 4-1BB. In a particular embodiment, the scFv is anti-ErbB2/HER2 receptor, anti-CD19, or anti-GD2.

In accordance with the instant invention, methods of inhibiting (e.g., reducing), preventing, and/or treating cancer are provided. In a particular embodiment, the method comprises administering chimeric antigen receptor T cells to the subject, wherein CBL and/or CBL-B is inhibited or reduced (e.g., as compared to wild-type or untreated), particularly wherein both CBL and CBL-B are inhibited or reduced. The administered T cells may be autologous. For example, the methods may comprise transducing T cells ex vivo with a nucleic acid encoding a chimeric antigen receptor and inhibitory nucleic acid molecules for CBL and CBL-B. The methods of the instant invention may further comprise obtaining the T cells from the subject to be treated.

The methods of the instant invention can be used to inhibit, prevent, and/or treat any cancer. In a particular embodiment, the cancer is a solid tumor. In a particular embodiment, the cancer is a hematological cancer. Examples of cancer that can be treated by the methods of the instant invention include, without limitation: leukemia (e.g., acute lymphoblastic leukemia, acute myeloid leukemia, chronic lymphocytic leukemia, chronic myelogenous leukemia), lymphoma (e.g., Hodgkin lymphoma, Non-Hodgkin lymphoma), multiple myeloma, breast cancer, prostate cancer, pancreatic cancer, colon cancer, thyroid cancer, bladder cancer, liver cancer, neuroblastoma, brain cancers (e.g., gliomas, meningiomas, pituitary adenomas etc.), lung cancer, ovarian cancer, stomach cancer, skin cancer (e.g., melanoma), cervical cancer, testicular cancer, kidney cancer, carcinoid tumors, and bone cancer.

The methods may further comprise the administration of at least one other cancer therapy to the subject. Examples of additional therapies include, without limitation: chemotherapies (chemotherapeutic agents), immunotherapies, cell therapies, targeted therapy (e.g., small molecule inhibitors, antibodies), and radiation therapy (e.g., external beam radiation, radiopharmaceuticals). The CAR-T therapy of the instant invention may be administered to a subject consecutively (e.g., before and/or after) and/or simultaneously with another therapy for treating, inhibiting, and/or preventing the cancer in the subject.

Nucleic acid molecules encoding the chimeric antigen receptor and/or CBL and/or CBL-B inhibitory nucleic acid molecules of the instant invention may be contained within one or more vectors (e.g., operably linked to a promoter and/or enhancer for expression in the desired cell type). The nucleic acid encoding a chimeric antigen receptor and the agent(s) (e.g., inhibitory nucleic acid molecule(s)) used to inhibit or reduce CBL and/or CBL-B may be delivered to the target T cells consecutively (e.g., before and/or after) and/or simultaneously. For example, the CBL and/or CBL-B inhibitory nucleic acid molecules may be delivered to a T cell already transduced with a nucleic acid molecule encoding the chimeric antigen receptor (e.g., a CAR-T cell). As another example, the CBL and/or CBL-B inhibitory nucleic acid molecules and a nucleic acid molecule encoding the chimeric antigen receptor are delivered to a T cell (e.g., at the same time or sequentially). In a particular embodiment, the CBL and/or CBL-B inhibitory nucleic acid molecules and the nucleic acid molecule encoding the chimeric antigen receptor are in the same vector. The vectors of the instant invention may further comprise a marker gene (e.g., a fluorescent marker (e.g., green fluorescent protein (GFP)).

The vectors for use in the instant invention may be DNA or RNA. The vector may be an integrating vector or a non-integrating vector. Examples of vectors include, without limitation, plasmids, phagemids, cosmids, and viral vectors. In a particular embodiment, the vector is a plasmid. Examples of viral vectors include, without limitation: a parvoviral vector, lentiviral vector (e.g., HIV, SIV, FIV, EIAV, Visna), adenoviral vector, adeno-associated viral vector (e.g., AAV1-9), herpes vector (HSV1-8), or a retroviral vector. The viral vector may be a pseudotyped viral vector.

The promoter of the vector may be constitutive or inducible. Examples of promoters include, without limitation: the immediate early cytomegalovirus (CMV) promoter, human elongation factor-la, simian virus 40 (SV40) early promoter, human immunodeficiency virus (HIV) long terminal repeat (LTR) promoter, MoMuLV promoter, an avian leukemia virus promoter, an Epstein-Barr virus immediate early promoter, a Rous sarcoma virus promoter, spllen focus forming virus (SFFV), mouse stem cell virus (MSCV), phosphoglycerate kinase alpha (PGK-alpha), and actin promoter. Examples of inducible promoters include, without limitation: doxycycline-inducible promoters and tetracycline-inducible promoter (e.g., contain one or more tetracycline response elements (TREs) that bind to reverse tetracycline Trans-Activator (rtTA)).

For ex vivo methods, the nucleic acid molecules (e.g., vectors) of the instant invention may be transferred into the desired target cell (e.g., T cell (e.g., CD8+ cytotoxic T cells)) by any physical, chemical, or biological means. Methods for transferring nucleic acid molecules into cells are well known in the art (see, e.g., Sambrook et al. (Molecular Cloning: A Laboratory Manual, Cold Spring Harbor Laboratory, New York). Exemplary methods of transferring the nucleic acid molecules into cells include, without limitation: transfection (non-viral), calcium phosphate precipitation, lipofection, particle bombardment, microinjection, electroporation, transposon-based systems (e.g., Sleeping Beauty (SB) and piggyback), infection (e.g., with viral vector (e.g., retroviral vectors (e.g., (e.g., gamma-retroviral and lentiviral vectors)))), and colloidal dispersion systems (e.g., nanocapsules, microspheres, micelles, and liposomes).

As stated hereinabove, the CBL and/or CBL-B inhibitory nucleic acid molecules and the nucleic acid molecule encoding the chimeric antigen receptor may be in the same vector. In a particular embodiment, the nucleic acid molecule encoding the chimeric antigen receptor is controlled by the CMV promoter. In a particular embodiment, the nucleic acid molecule encoding the CBL and/or CBL-B inhibitory nucleic acid molecules (e.g., shRNA) are controlled by an inducible promoter, particularly a doxycycline-inducible promoter.

Figure 2A:
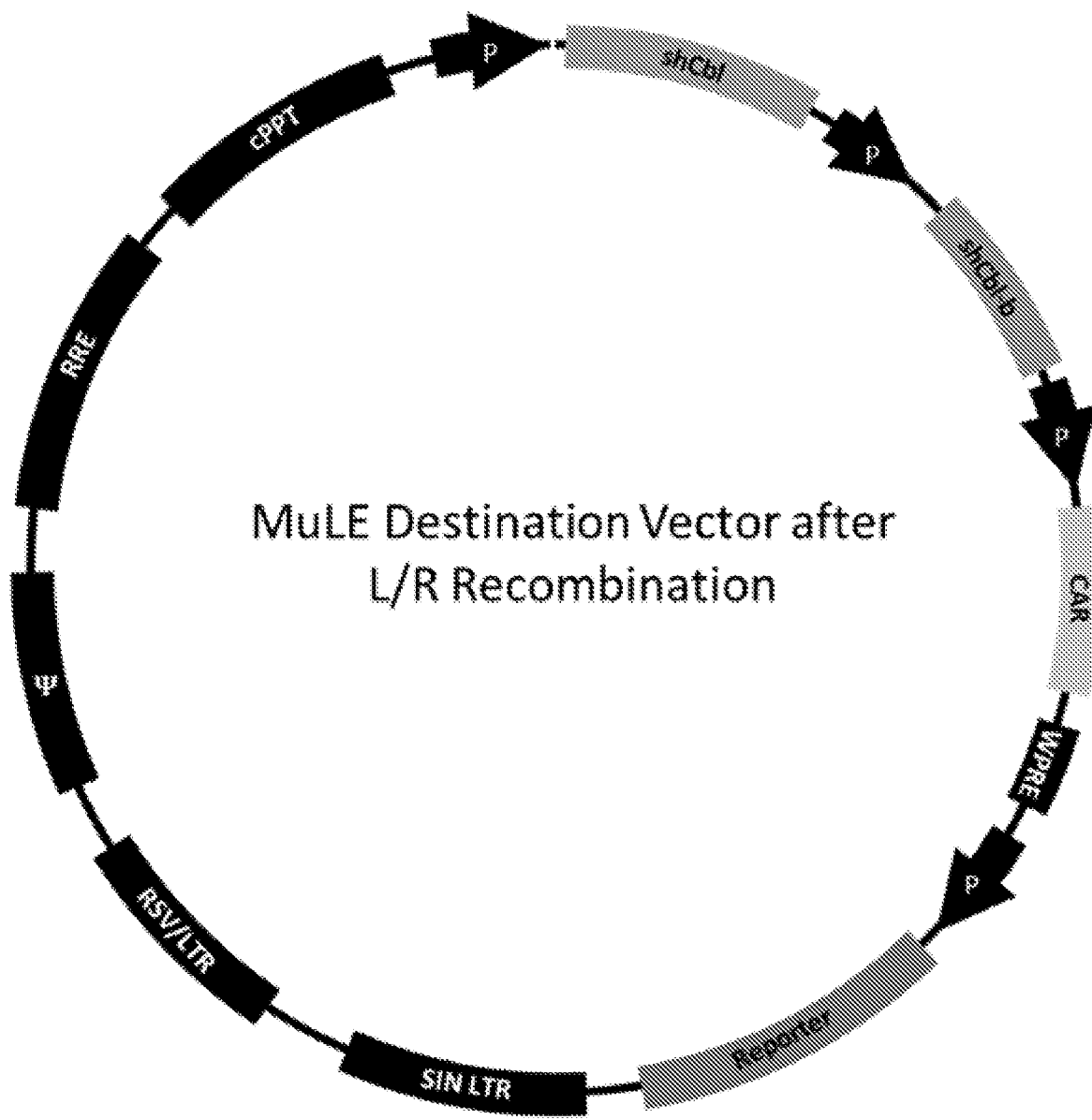
FIGS. 2A and 2B provide schematics of Hyper-CAR constructs.
Figure 2B:
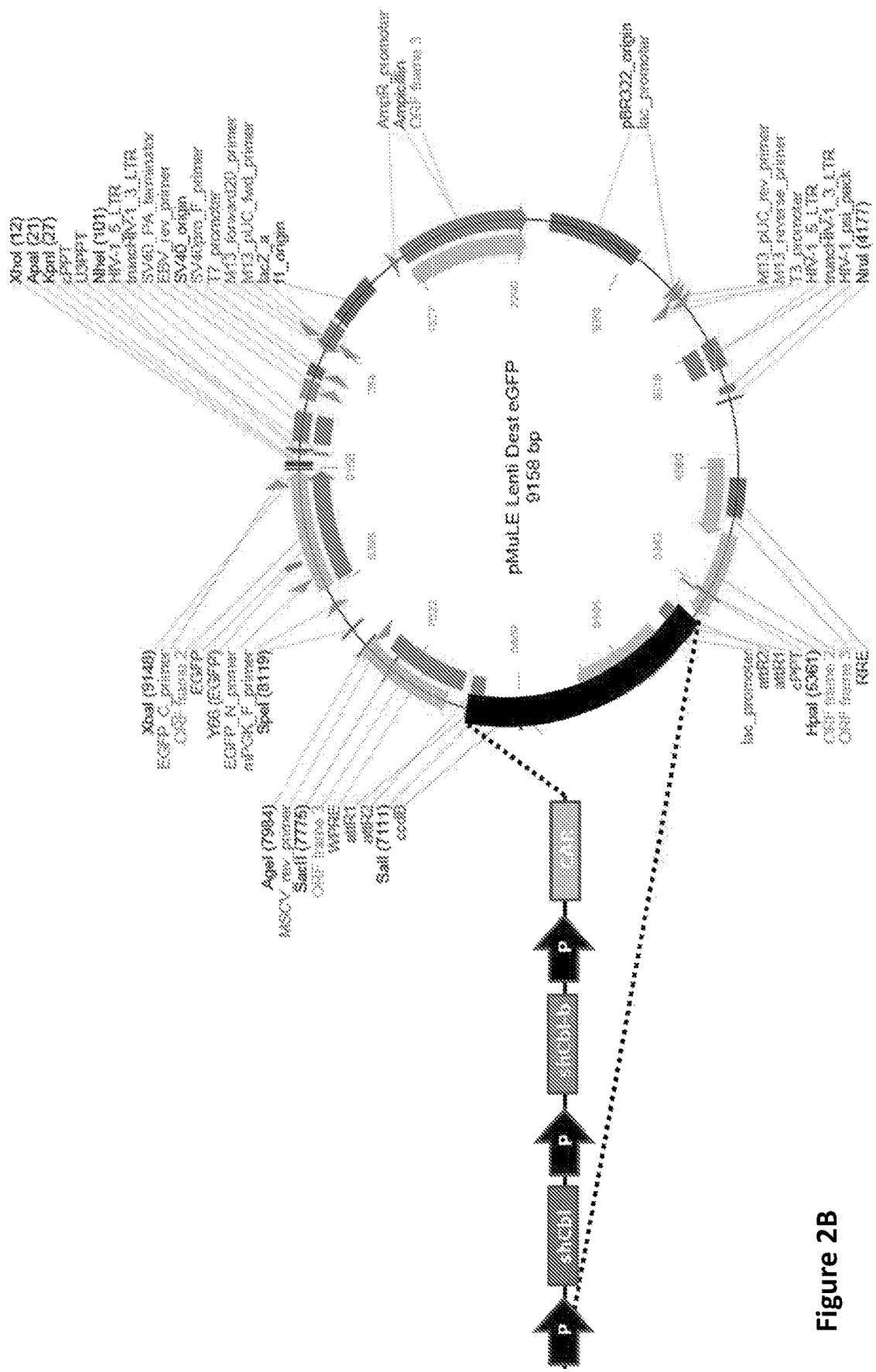

In a particular embodiment, the vector is a pMULE vector. The pMULE vector system is a versatile modular vector system for rapid combinatorial mammalian genetics. The pMULE vector system is described in Alders et al. (J. Clin. Invest. (2015) 125:1603-1619 and is available from Addgene (Cambridge, MA) (addgene.org/kits/mule-system). FIG. 1 provides a schematic of an example sequential assembly of shRNA elements against Cbl and Cbl-b together with a chimeric antigen receptor to derive a Hyper-CAR expression construct with a reporter (e.g., GFP) for selection of T-cells successfully transduced after lentiviral-mediated infection. FIGS. 2A and 2B provide schematics of the Hyper-CAR construct. In a particular embodiment, shRNA sequences directed at human CBL and CBL-B and specific CAR sequences are first cloned into pMule entry vectors followed by LR clonase-based combination into a polycistronic third-generation lentiviral destination vector, optionally containing a reporter such as a selectable fluorescent marker (e.g., GFP). More specifically, a nucleic acid molecule encoding the chimeric antigen receptor can be cloned into a CMV promoter-drive pMULE entry vector (pMULE ENTR CMV L3-L2; addgene.org/62092/sequences) to generate a single open reading frame coding for the CAR. Two additional amino acids (Gly/Ser) may be added between the two segments from the restriction enzyme sequences (GGATCC) used to clone the gene segments. Cbl and Cbl-b shRNAs can be cloned into the doxycycline-inducible miR-30-based shRNA expressing pMULE entry vectors pMULE ENTR CMV/TO-miR-30 L1-L4 (addgene.org/62124/sequences) and pMULE ENTR CMV/TO-miR-30 R4-R3 (addgene.org/62125/sequences). LR cloning may be performed to transfer these entry vectors into a modular lentiviral destination vector (pMULE Lenti Dest eGFP). For the particular Cbl and Cbl-b shRNA sequences, the miRE adaptor sequences (Fellman et al. (2013) Cell Reports 5:1-10) replace the miR-30 sequences in the pMULE destination vectors. For doxycycline-inducible expression of shRNAs, an rtTA element is cloned upstream of the promoter in the pMULE destination vector. Alternate vector systems for DOX-inducible shRNA include SMARTvector® Inducible Lentiviral shRNA (Dharmacon), pTRIPZ lentiviral vector (Dharmacon), Tet-PLKO-puro (Addgene), pInducer20 (Addgene).

As stated hereinabove, the vectors may comprise a reporter such as a fluorescent marker (e.g., GFP) which allows for the selection of transduced T cells (e.g., CD8+ cytotoxic T cells) (e.g., by FACS) or using drug selection markers (e.g., puromycin or neomycin). The selected T cells may also be expanded (e.g., using anti-CD3 antibody beads). The depletion of CBL and CBL-B allows T cell proliferation in the presence of anti-CD3 antibody alone, thereby providing a further selective enrichment of T cells with CBL/CBL-B depletion. Due to their hyperactive phenotype, Hyper-CAR-T cells also provide a higher yield from a smaller number of patient cells during in vitro expansion. Therefore, sufficient CAR-T cells can be obtained more rapidly and can be obtained even in lymphopenic patients.

Additional elements can be included in the vector design to impart safety against possible toxicity of Hyper-CAR-T cells. Such elements can include the insertion of a suicide gene in the vector that can be activated in an inducible manner. Examples of such elements include the insertion of the herpes simplex virus thymidine kinase (HSV-TK) gene which allows the elimination of CAR-T cells bearing this cassette upon treatment with ganciclovir (Ciceri et al. (2009) Lancet Oncol., 10:489-500) or placement of an inducible caspase 9 (iCasp9) gene, a fusion of pro-apoptotic human caspase 9 to a modified human FK-binding protein allowing conditional dimerization and induction by a drug AP1903 (Di Stasi A et al. (2011) N. Engl. J. Med., 365(18):1673-83).

In accordance with another aspect of the instant invention, compositions comprising at least one nucleic acid molecule of the instant invention and a least one carrier are provided. Kits comprising at least one first composition comprising at least one nucleic acid encoding a chimeric antigen receptor of the instant invention and at least one second composition comprising at least one agent for reducing and/or inhibiting CBL and/or CBL-B of the instant invention (e.g., at least one other inhibitor of CBL and/or CBL-B) are also encompassed by the instant invention. The instant invention also encompasses compositions comprising the CAR-T cells of the instant invention (e.g., Hyper-CAR-T cells) and at least one pharmaceutically acceptable carrier.

The compositions of the present invention (e.g., compositions comprising CAR-T cells of the instant invention) can be administered by any suitable route, for example, by injection (e.g., for local (direct, including to or within a tumor) or systemic administration), oral, pulmonary, topical, nasal or other modes of administration. The composition may be administered by any suitable means, including parenteral, intramuscular, intravenous, intraarterial, intraperitoneal, subcutaneous, topical, inhalatory, transdermal, intrapulmonary, intraareterial, intrarectal, intramuscular, and intranasal administration. In a particular embodiment, the composition is administered to the blood (e.g., intravenously). In a particular embodiment, the composition is administered locally to the desired site. For example, the composition may be administered by intratumoral injection or by injection near the tumor site. In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., Tween® 80, polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention (e.g., Remington: The Science and Practice of Pharmacy). The pharmaceutical composition of the present invention can be prepared, for example, in liquid form, or can be frozen (e.g., with the addition of at least one cell-freezing component (e.g., DSMO, serum, cell culture medium, etc.) and placement in liquid nitrogen.

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the molecules to be administered, its use in the pharmaceutical preparation is contemplated.

The dose and dosage regimen of the molecule of the invention that is suitable for administration to a particular patient may be determined by a physician considering the patient's age, sex, weight, general medical condition, and the specific condition and severity thereof for which the inhibitor is being administered. The physician may also consider the route of administration, the pharmaceutical carrier, and the molecule's biological activity.

Selection of a suitable pharmaceutical preparation depends upon the method of administration chosen. For example, the molecules of the invention may be administered by direct injection into any cancerous tissue or into the area surrounding the cancer. In this instance, a pharmaceutical preparation comprises the molecules dispersed in a medium that is compatible with the cancerous tissue.

Pharmaceutical compositions of the present invention can be prepared according to conventional pharmaceutical compounding techniques. The carrier may take a wide variety of forms depending on the form of preparation desired for administration, e.g., intravenous, oral, topical, or parenteral. For parenterals, the carrier will usually comprise sterile water and salts (e.g., saline), though other ingredients, for example, to aid solubility or for preservative purposes, may be included. Injectable suspensions may also be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight/surface area of the patient. Appropriate concentrations for alleviation of a particular pathological condition may be determined by dosage concentration curve calculations, as known in the art. The appropriate dosage unit for the administration of the molecules of the instant invention may be determined by evaluating the toxicity of the molecules in animal models. Various concentrations of pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the treatment in combination with other standard chemotherapies. The dosage units of the molecules may be determined individually or in combination with each chemotherapy or other form of therapy according to greater shrinkage and/or reduced growth rate of tumors.

The pharmaceutical preparation comprising the molecules of the instant invention may be administered at appropriate intervals, for example, at least every four weeks or more until the pathological symptoms are reduced or alleviated, after which the dosage may be reduced to a maintenance level. The appropriate interval in a particular case would normally depend on the condition of the patient.

Definitions

The following definitions are provided to facilitate an understanding of the present invention:

The singular forms "a," "an," and "the" include plural referents unless the context clearly dictates otherwise.

As used herein, the terms "host," "subject," and "patient" refer to any animal, particularly mammals including humans.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween® 80, polysorbate 80), emulsifier, buffer (e.g., Tris HCl, acetate, phosphate), antimicrobial, bulking substance (e.g., lactose, mannitol), excipient, auxilliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in, for example, Remington: The Science and Practice of Pharmacy; Liberman, et al., Eds., Pharmaceutical Dosage Forms; and Rowe, et al., Eds., Handbook of Pharmaceutical Excipients.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition (e.g., cancer) resulting in a decrease in the probability that the subject will develop the condition.

A "therapeutically effective amount" of a compound or a pharmaceutical composition refers to an amount effective to prevent, inhibit, or treat a particular disorder or disease and/or the symptoms thereof.

As used herein, the term "subject" refers to an animal, particularly a mammal, particularly a human.

As used herein, the term "small molecule" refers to a substance or compound that has a relatively low molecular weight (e.g., less than 4,000, particularly less than 2,000). Typically, small molecules are organic, but are not proteins, polypeptides, or nucleic acids, though they may be amino acids or dipeptides.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule. The term includes polyclonal, monoclonal, chimeric, single domain (Dab) and bispecific antibodies. As used herein, antibody or antibody molecule contemplates recombinantly generated intact immunoglobulin molecules and molecules comprising immunologically active portions of an immunoglobulin molecule such as, without limitation: Fab, Fab', F(ab')$_2$, F(v), scFv, scFv$_2$, scFv-Fc, minibody, diabody, tetrabody, and single variable domain (e.g., variable heavy domain, variable light domain). Methods of making antibodies directed toward a target polypeptide or protein or fragment thereof (e.g., epitope) are well known in the art.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

The term "vector" refers to a carrier nucleic acid molecule (e.g., DNA) into which a nucleic acid sequence can be inserted for introduction into a host cell where it will be replicated. The vector may contain a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.), particularly at least 75% by weight, or at least 90-99% or more by weight of the compound of interest. Purity may be measured by methods appropriate for the compound of interest (e.g. chromatographic methods, agarose or polyacrylamide gel electrophoresis, HPLC analysis, and the like). Purity for CAR-T cells may comprise of the percentage of infused CAR-T cells that express the CAR (e.g., determined by FACS) and that express the shRNA (e.g., determined by the level of reduction in CBL or CBL-B expression as assessed by qPCR, FACS or Western blotting).

As used herein, a "linker" is a chemical moiety comprising a covalent bond or a chain of atoms that covalently attaches two molecules to each other. In a particular embodiment, the linker comprises amino acids, particularly from 1 to about 25, 1 to about 20, 1 to about 15, or 1 to about 10 amino acids.

The phrase "small, interfering RNA (siRNA)" refers to a short (typically less than 30 nucleotides long, particularly 12-30 or 20-25 nucleotides in length) double stranded RNA molecule. Typically, the siRNA modulates the expression of a gene to which the siRNA is targeted. Methods of identifying and synthesizing siRNA molecules are known in the art (see, e.g., Ausubel et al. (2006) Current Protocols in Molecular Biology, John Wiley and Sons, Inc). As used herein, the term siRNA may include short hairpin RNA molecules (shRNA). Typically, shRNA molecules consist of short complementary sequences separated by a small loop sequence wherein one of the sequences is complimentary to the gene target. shRNA molecules are typically processed into an siRNA within the cell by endonucleases. Exemplary modifications to siRNA molecules are provided in U.S. Application Publication No. 20050032733. Expression vectors for the expression of shRNA or siRNA molecules preferably employ a strong promoter which may be constitutive or regulated. Such promoters are well known in the art and include, but are not limited to, RNA polymerase II promoters and the RNA polymerase III promoters U6 and H1 (see, e.g., Myslinski et al. (2001) Nucl. Acids Res., 29:2502 09).

"Antisense nucleic acid molecules" or "antisense oligonucleotides" include nucleic acid molecules (e.g., single stranded molecules) which are targeted (complementary) to a chosen sequence (e.g., to translation initiation sites and/or splice sites) to inhibit the expression of a protein of interest. Such antisense molecules are typically between about 15 and about 50 nucleotides in length, more particularly between about 15 and about 30 nucleotides, and often span the translational start site of mRNA molecules. Antisense constructs may also be generated which contain the entire sequence of the target nucleic acid molecule in reverse orientation. Antisense oligonucleotides targeted to any known nucleotide sequence can be prepared by oligonucleotide synthesis according to standard methods.

The term "CRISPR" refers to Clustered, regularly interspaced, short palindromic repeat. CRISPR/Cas9 (e.g., from *Streptococcus pyogenes*) technology and gene editing are well known in the art (see, e.g., Sander et al. (2014) Nature Biotech., 32:347-355; Jinek et al. (2012) Science, 337:816-821; Cong et al. (2013) Science 339:819-823; Ran et al. (2013) Nature Protocols 8:2281-2308; Mali et al. (2013) Science 339:823-826; addgene.org/crispr/guide/). The RNA-guided CRISPR/Cas9 system involves expressing Cas9 along with a guide RNA molecule (gRNA), which is specific to a target sequence or gene. When coexpressed, gRNAs bind and recruit Cas9 to a specific genomic target sequence where it mediates a double strand DNA (dsDNA) break. Guidelines and computer-assisted methods for generating gRNAs are available (see, e.g, CRISPR Design Tool (crispr.mit.edu/); Hsu et al. (2013) Nat. Biotechnol. 31:827-832; addgene.org/CRISPR; and CRISPR gRNA Design tool—DNA2.0 (dna20.com/eCommerce/startCas9)).

The term "TALEN" refers to transcription activator-like effector nucleases. These nucleases comprise a TAL-effector domain fused to a nuclease domain. TAL-effector DNA binding domains are from *Xanthomonas* bacteria and have been described (see, e.g., Boch et al. (2009) Science 326 (5959):1509-12; Moscou et al. (2009) Science 326(5959): 1501). These DNA binding domains may be engineered to bind to a desired target and fused to a nuclease domain, such as the Fok1 nuclease domain, to derive a TAL effector domain-nuclease fusion protein.

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, and *Pseudomonas* exotoxin); taxanes; alkylating agents (e.g., temozolomide, nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes (e.g., cisplatin, carboplatin, tetraplatin, ormaplatin, thioplatin, satraplatin, nedaplatin, oxaliplatin, heptaplatin, iproplatin, transplatin, and lobaplatin); bioreductive alkylators such as mitomycin, procarbazine, dacarbazine and altretamine); DNA strand-breakage agents (e.g., bleomycin); topoisomerase II inhibitors (e.g., amsacrine, menogaril, amonafide, dactinomycin, daunorubicin, N,N-dibenzyl daunomycin, ellipticine, daunomycin, pyrazoloacridine, idarubicin, mitoxantrone, m-AMSA, bisantrene, doxorubicin (adriamycin), deoxydoxorubicin, etoposide (VP-16), etoposide phosphate, oxanthrazole, rubidazone, epirubicin, bleomycin, and teniposide); DNA minor groove binding agents (e.g., plicamydin); antimetabolites (e.g., folate antagonists such as methotrexate and trimetrexate); pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); anthracyclines; and tubulin interactive agents (e.g., vincristine, vinblastine, and paclitaxel (Taxol®)).

Radiation therapy refers to the use of high-energy radiation from x-rays, gamma rays, neutrons, protons and other sources to target cancer cells. Radiation may be administered externally, or it may be administered using radioactive material given internally. Chemoradiation therapy combines chemotherapy and radiation therapy.

As used herein, the term "kit" refers to an assembly or a packaged combination of materials and/or reagents.

The following example is provided to illustrate certain embodiments of the invention. It is not intended to limit the invention in any way.

EXAMPLE

A general design of one of the constructs can be: RE-Kozak sequence-CD8 leader-scFv($V_L$-linker-$V_H$)-modified human IgG1-RE. RE represents unique restriction enzyme sequences for directional cloning (e.g., AAGCTT in FIGS. 3A, 3C, and 3E). Kozak sequence represents a consensus Kozak sequence including specific nucleotides before and after the initiation codon (ATG) introduced for efficient protein translation when expressed in T cells (e.g., GCCACCATGG (SEQ ID NO: 28) in FIGS. 3A, 3C, and 3E). CD8 leader represents the leader (signal) peptide sequence from human CD8-alpha for endoplasmic reticulum membrane entry of the encoded transmembrane CAR polypeptide (e.g., CCTTA . . . GGCGG in FIGS. 3A, 3C, and 3E). scFv represents the single-chain variable fragment of any monoclonal antibody (e.g., mouse monoclonal) against a specific human tumor cell surface antigen. The scFv comprises $V_L$ (variable region of the immunoglobulin light chain) (e.g., GATAT . . . TCAAA in FIG. 3A; GACAT . . . GTAAT in FIG. 3C; GAGAA . . . TCAAG in FIG. 3E) and $V_H$ (variable region of the immunoglobulin heavy chain) (e.g., GAGGT . . . CCTCG in FIG. 3A; GAGGT . . . CCTCA in FIG. 3C; CAGGT . . . GCAGC in FIG. 3E) segments of the antibody separated by a flexible artificial linker (e.g., GGTGG . . . GCTCC in FIGS. 3A, 3C, and 3E). Modified human IgG1 represents sequences coding for the constant region of human IgG1 (e.g., GAGCC . . . GTAAA in FIGS. 3A, 3C, and 3E). Modifications include changing amino acids PELLGG (SEQ ID NO: 19) (nucleotides CCTGAACTCCTGGGGGGA (SEQ ID NO: 20)) to PPVAG (SEQ ID NO: 21) (nucleotides CCTCCAGTCGCGGGA (SEQ ID NO: 22)) and amino acids ISR (nucleotides ATCTCCCGG) to amino acids IAR (nucleotides ATCGCCCGG). These modifications eliminate the Fc receptor binding of the IgG1 in order to minimize any non-specific cytotoxicity of CAR-T cells (Hombach et al. (2010) Gene Therapy 17:1206-1213).

FIG. 3A provides a DNA sequence of this construct for anti-ErbB2/HER2 receptor CAR based on antibody 4D5 (Carter et al. (1992) Proc. Natl. Acad. Sci. 89:4285-4289). FIG. 3B provides an amino acid sequence of this construct for anti-ErbB2/HER2 receptor CAR based on antibody 4D5. FIG. 3C provides a DNA sequence of this construct for anti-CD19 CAR based on a mouse monoclonal anti-CD19 antibody (Nicholson et al. (1997) 34:1157-1165). FIG. 3D provides an amino acid sequence of this construct for anti-CD19 CAR. FIG. 3E provides a DNA sequence of this construct for anti-GD2 CAR based on a mouse monoclonal anti-GD2 antibody huKM666 (Nakamura et al. (2001) 50:275-284). FIG. 3F provides an amino acid sequence of this construct for anti-GD2 CAR.

A general design for a second construct of the instant invention can be: RE-CD28-4-1BB-CD3 zeta-STOP-RE. RE represents unique restriction enzyme sequences for directional cloning (e.g., GGATCC in FIG. 3G). CD28 represents transmembrane domain and cytoplasmic region (e.g., TTTG . . . GCTCC in FIG. 3G). 4-1BB is a cytoplasmic sequence (e.g., AAACG . . . AACTG in FIG. 3G). CD3 zeta is a cytoplasmic sequence followed by a stop codon (e.g., AGAGT . . . GCTAA in FIG. 3G). FIG. 3G provides a DNA sequence of this construct with human CD28, 4-1BB, and CD3 zeta. FIG. 3H provides an amino acid sequence of this construct.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. Isolated T cells comprising a nucleic acid molecule encoding a chimeric antigen receptor, wherein said T cells comprise at least one inhibitory nucleic acid molecule for CBL and at least one inhibitory nucleic acid molecule for CBL-B, and wherein the expression of CBL and CBL-B is inhibited in said T cells, wherein said inhibitory nucleic acid molecule for CBL and said inhibitory nucleic acid molecule for CBL-B are selected from the group consisting of antisense, siRNA, shRNA, and miRNA, wherein said chimeric antigen receptor comprises SEQ ID NO: 2, SEQ ID NO: 4, or SEQ ID NO: 6, wherein said inhibitory nucleic acid molecule for CBL comprises or is complementary to a nucleotide sequence selected from the group consisting of AGCAGCTAGTATGTTTTATTAT (SEQ ID NO: 11), TCAGTGGTTCCAAGATTTCAA (SEQ ID NO: 12), and GGCGAAACCTAACCAAACT (SEQ ID NO: 13):

wherein said inhibitory nucleic acid molecule for CBL-B comprises or is complementary to a nucleotide sequence selected from the group consisting of: AGGTGAAAATGTCAAAACTAA (SEQ ID NO: 16), CAGTGAGAATGAGTACTTTA (SEQ ID NO: 17), and GACCATACCTCATAACAAG (SEQ ID NO: 18).

2. The isolated T cells of claim 1, wherein said inhibitory nucleic acid molecule for CBL and said inhibitory nucleic acid molecule for CBL-B are siRNA or a shRNA.

3. A composition comprising the isolated T cells of claim 1 and at least one pharmaceutically acceptable carrier.

4. The isolated T cells of claim 2, wherein said inhibitory nucleic acid molecule for CBL and said inhibitory nucleic acid molecule for CBL-B are shRNA.

5. The isolated T cells of claim 4, wherein said inhibitory nucleic acid molecule for CBL-B is a shRNA which comprises SEQ ID NO: 15.

6. The isolated T cells of claim 1, wherein said nucleic acid molecule encoding the chimeric antigen receptor comprises SEQ ID NO: 1.

7. The isolated T cells of claim 1, wherein said chimeric antigen receptor comprises SEQ ID NO: 2.

8. The isolated T cells of claim 1, wherein said chimeric antigen receptor comprises SEQ ID NO: 4 or SEQ ID NO: 6.

* * * * *